United States Patent
Biolchini, Jr.

(10) Patent No.: US 7,824,425 B2
(45) Date of Patent: Nov. 2, 2010

(54) AMBIDEXTROUS LOCKING CLAMP SYSTEM

(76) Inventor: Robert F. Biolchini, Jr., 692 E. Hansen P.O. Box 613, Jackson, WY (US) 83001

(*) Notice: Subject to any disclaimer, the term of this patent is extended or adjusted under 35 U.S.C. 154(b) by 1389 days.

(21) Appl. No.: 11/252,159

(22) Filed: Oct. 17, 2005

(65) Prior Publication Data
US 2007/0167977 A1    Jul. 19, 2007

Related U.S. Application Data

(63) Continuation-in-part of application No. 10/909,623, filed on Aug. 2, 2004.

(51) Int. Cl.
*A61B 17/28* (2006.01)
*A61B 17/29* (2006.01)

(52) U.S. Cl. ............................ 606/208; 606/205

(58) Field of Classification Search ......... 606/205–210, 606/135; 81/300, 302, 315, 318–320, 324–328; 30/232, 254, 256, 262, 341, 194, 251; 16/105–130; 294/82.1–120; 292/256–278
See application file for complete search history.

(56) References Cited

U.S. PATENT DOCUMENTS

| | | | |
|---|---|---|---|
| 3,417,752 A * | 12/1968 | Butler | .................. 606/147 |
| 3,913,586 A | 10/1975 | Baumgarten | |
| 3,978,584 A | 9/1976 | Mayer | |
| 4,452,246 A * | 6/1984 | Bader et al. | .................. 606/147 |
| 4,823,792 A * | 4/1989 | Dulebohn et al. | ........... 606/151 |
| 5,176,702 A | 1/1993 | Bales | |
| 5,626,608 A | 5/1997 | Cuny | |
| 6,223,440 B1 | 5/2001 | Rashman | |
| 6,397,478 B1 | 6/2002 | Bornancini | |
| 2004/0106947 A1 | 6/2004 | Propp | |

* cited by examiner

*Primary Examiner*—Anhtuan T Nguyen
*Assistant Examiner*—Amy T Lang
(74) *Attorney, Agent, or Firm*—David A. Guerra

(57) ABSTRACT

An ambidextrous locking clamp system for providing a user the ability to alter the configuration of a hand operated device allowing a right or left handed user to operate the device. The device has a hingedly connected first and second elongated member each with a finger engaging member, a working head, and an indicator for identifying if the clamp is setup for left or right handed operation. At least two inter-engaging latching members are removably attachable to the first and the second elongated members. The latching members are symmetrical, interchangeable, and reversible, allowing a user to change the configuration of the ambidextrous device. The latching members can be retained to the elongated members by a rotatably lever, a removable retaining cap, or a removable retaining pin. Additionally, the latching members can be incorporated into removable finger engaging members, thereby allowing the entire finger engaging member and latching member to be removed, interchanged or reversed.

20 Claims, 28 Drawing Sheets

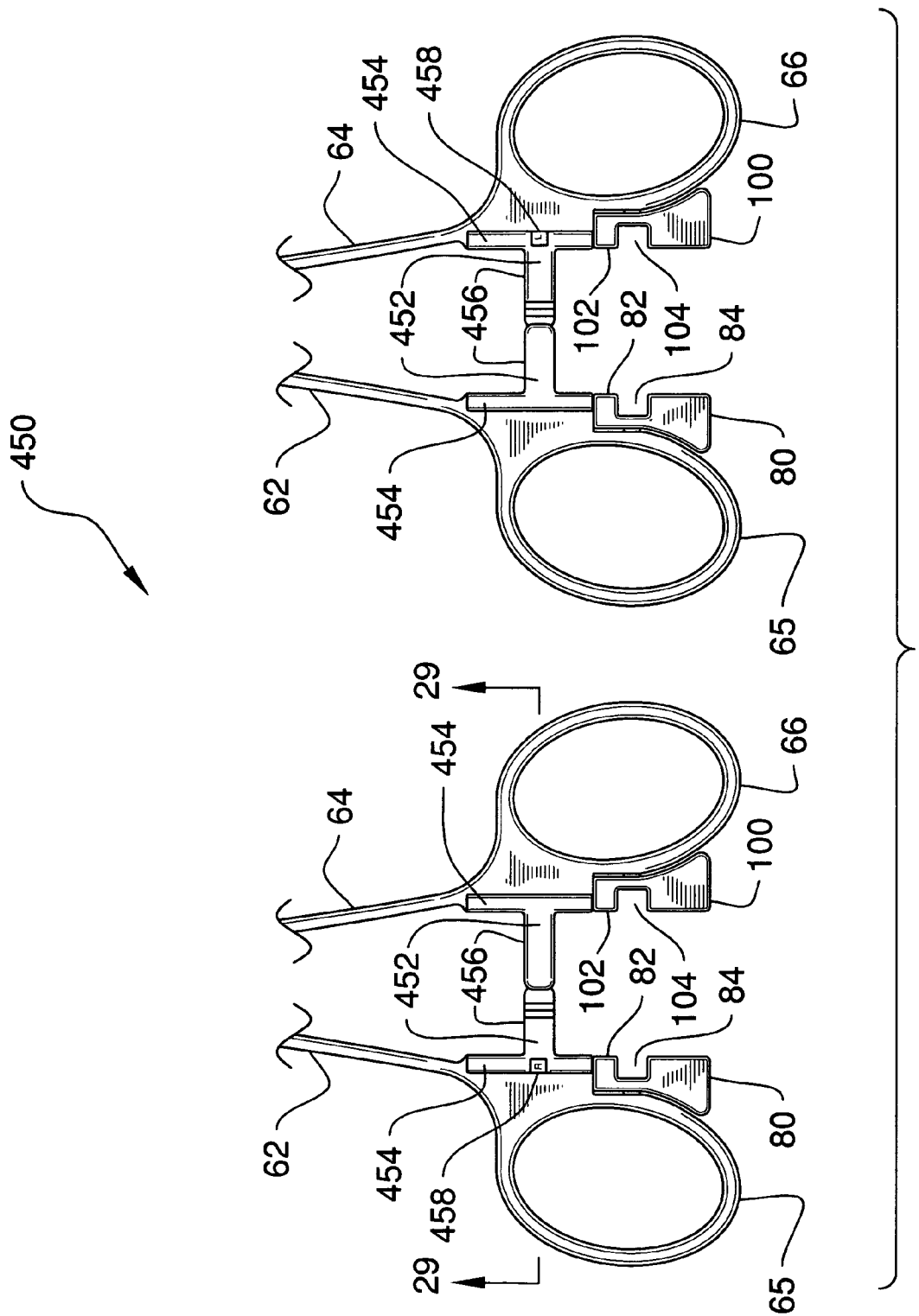

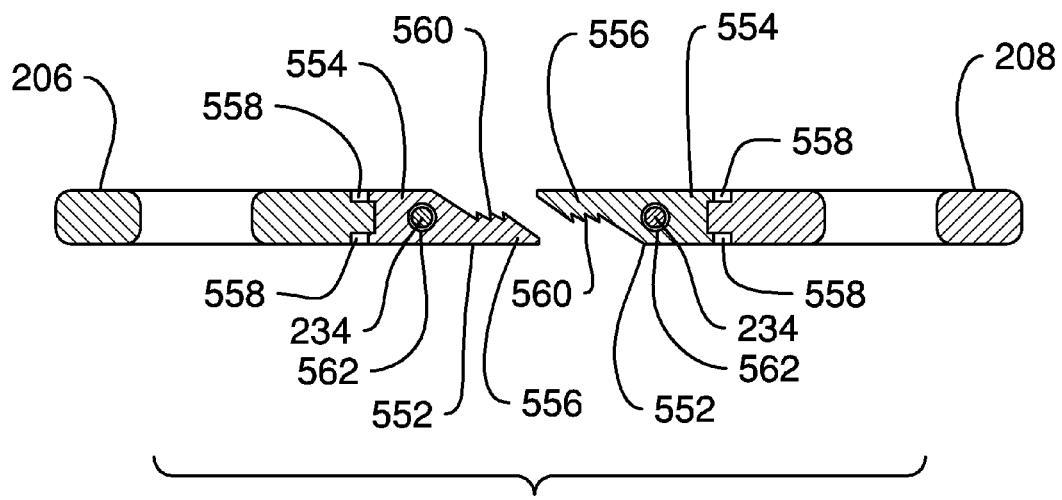
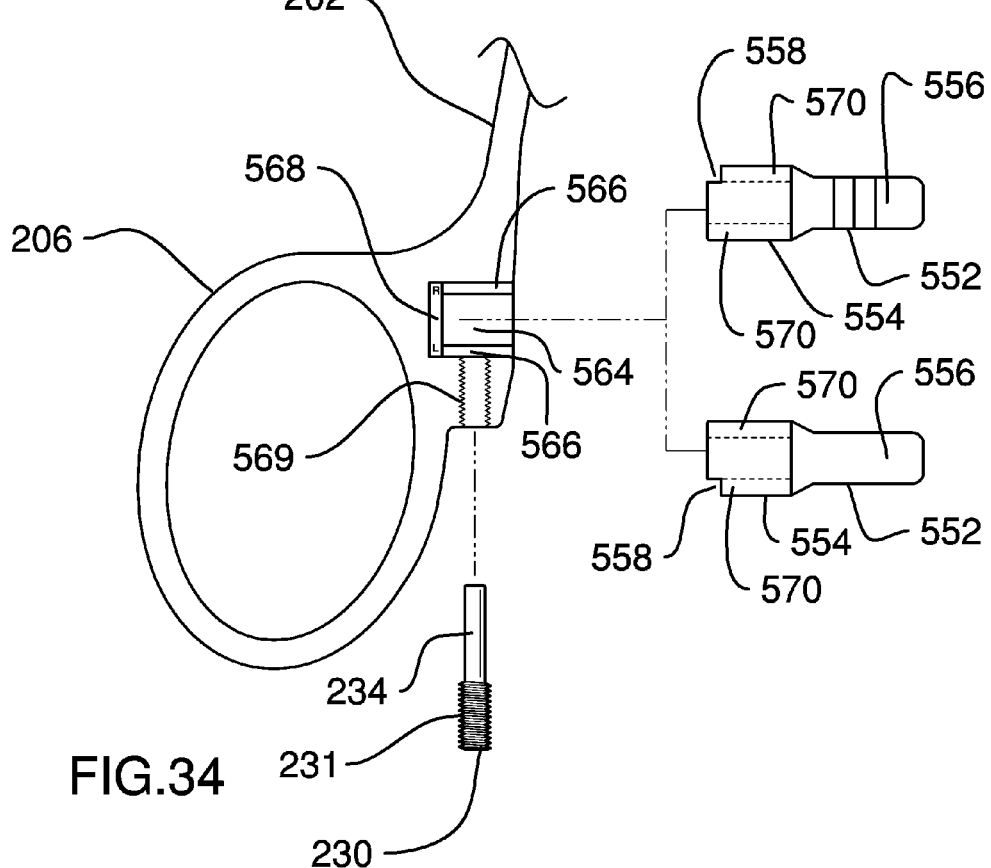
FIG. 35
FIG. 34

AMBIDEXTROUS LOCKING CLAMP SYSTEM

CROSS REFERENCE TO RELATED APPLICATION

This application is a continuation-in-part of U.S. patent application Ser. No. 10/909,623, filed Aug. 2, 2004. All prior applications are hereby incorporated by reference in their entireties.

BACKGROUND OF THE INVENTION

1. Field of the Invention

The present invention relates to an ambidextrous locking clamp system for use in connection with clamping instruments, such as surgical clamps, forceps, or hemostats. The ambidextrous locking clamp system has particular utility in connection with manipulating objects with a tool having removable and interchangeable locking assemblies.

2. Description of the Prior Art

Ambidextrous locking clamps, forceps or hemostats are desirable for allowing a right or left-handed user to use a single hand operated clamp, forceps or hemostat device. These hand operated devices have been manufactured in the past for either a right hand or left hand user. This manufacturing process has some disadvantages in that the manufacturer would have to make a decision to how many right handed and left handed devices to fabricate. In most cases the decision is made to manufacture more right-handed devices than left handed devices. Therefore, it is well known that it is very difficult for a left-handed user to operate a right-handed device.

Hand operated locking clamps, forceps, and hemostats are well known. These devices include a pair of elongated members joined by a hinge. The hinge is usually a hinge pin extending through both elongated members. One end of the elongated members features a working head, usually a gripping jaw or cutting edges. The other end of the elongated members feature a finger engaging loop, with a set of ratchet teeth extending out therefrom towards the ratchet teeth of the finger loop of the second elongated member. The ratchet teeth are orientated so that they engage each other when the finger loop ends are brought together. These devices are mainly used in the medical industry for a wide variety of uses, but they are also used in the fly fishing, model building, and electrical industries.

During operation of a standard right handed hand operated device, the user inserts his or her thumb into one loop, the middle finger in the opposite loop, and the index finger would rest on the top of the middle finger loop for support and control of the device. To engage the working head the user squeezes the thumb and middle finger together guided by the index finger. The device is locked in the close position by further squeezing the loops together until the ratchet teeth members engage each other. To release, the thumb pushes away from the palm of the hand and the middle finger pulls toward the palm of the hand. This motion makes the ratchet teeth members flex away from each other and disengage.

The difficulty lies when a left-handed user tries to operate a right-handed device. It is difficult for a left-handed user to pull with the thumb and push with the middle finger. This is not a natural hand motion.

The use of locking clamps is known in the prior art. For example, U.S. Pat. No. 6,397,478 to Jose Carlos Mario Bornancini; U.S. Pat. No. 3,978,584 to John Mayer; U.S. Pat. No. 3,913,586 to Baumgarten; U.S. Pat. No. 6,223,440 to Rashman; United States Patent Application Publication 2004/0106947 to Propp et al.; U.S. Pat. No. 5,626,608 Cuny et al.; and U.S. Pat. No. 5,176,702 to Bales et al.

While the above-described devices fulfill their respective, particular objectives and requirements, the aforementioned patents do not describe an ambidextrous hand operated device that allows the use of the device by a right or left handed user through the interchanging of components.

Therefore, a need exists for a new and improved ambidextrous locking clamp system that can be used for manipulating objects with a tool having removable and interchangeable components. In this regard, the present invention substantially fulfills this need. In this respect, the ambidextrous locking clamp system according to the present invention substantially departs from the conventional concepts and designs of the prior art, and in doing so provides an apparatus primarily developed for the purpose of manipulating objects with a tool having removable and interchangeable locking assemblies.

SUMMARY OF THE INVENTION

In view of the foregoing disadvantages inherent in the known types of hand operated locking devices now present in the prior art, the present invention provides an improved ambidextrous locking clamp system, and overcomes the above-mentioned disadvantages and drawbacks of the prior art. As such, the general purpose of the present invention, which will be described subsequently in greater detail, is to provide a new and improved ambidextrous locking clamp system and method which has all the advantages of the prior art mentioned heretofore and many novel features that result in a ambidextrous locking clamp system which is not anticipated, rendered obvious, suggested, or even implied by the prior art, either alone or in any combination thereof.

To attain this, the present invention essentially comprises an ambidextrous locking clamp system for providing a user the ability to alter the configuration of a hand operated device allowing a right hand or left hand user to operate the device, wherein the ambidextrous locking clamp system has a first elongated member including a working head and a finger engaging member including an indicator for identifying a first side, a second elongated member including a working head and a finger engaging member including an indicator for identifying a second side, wherein the second elongated member is hingedly connected to the first elongated member, and at least two latching members having notches for viewing the indicators, wherein the latching members are removably attachable to the first and second elongated members.

Additionally, the present invention may comprise an ambidextrous locking clamp system having a first elongated member including a finger engaging member receiving assembly and a working head opposite of the finger engaging member receiving assembly, a second elongated member including a finger engaging member receiving assembly and a working head opposite of the finger engaging member receiving assembly, at least two finger engaging members removably attachable to the finger engaging member receiving assemblies of the first and second elongated members, and at least two retaining caps for retaining the finger engaging members to the finger engaging member receiving assemblies. The second elongated member is hingedly connected to the first elongated member. Furthermore, the finger engaging member receiving assemblies have an indicator and the finger engaging members have a notch that is positionable over the indicator.

There has thus been outlined, rather broadly, the more important features of the invention in order that the detailed description thereof that follows may be better understood and in order that the present contribution to the art may be better appreciated.

The invention may also include a variety of means to retain the latching members to the first and second elongated members, such as, but not limited to, rotating levers, removable retaining caps, and removable retaining pins. There are, of course, additional features of the invention that will be described hereinafter and which will form the subject matter of the claims attached.

Numerous embodiments, features and advantages of the present invention will be readily apparent to those of ordinary skill in the art upon a reading of the following detailed description of presently preferred, but nonetheless illustrative, embodiments of the present invention when taken in conjunction with the accompanying drawings. In this respect, before explaining the current embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an embodiment of the present invention to provide a new and improved ambidextrous locking clamp system that has all of the advantages of the prior art locking clamps and none of the disadvantages.

It is another embodiment of the present invention to provide a new and improved ambidextrous locking clamp system that may be easily and efficiently manufactured and marketed.

An even further embodiment of the present invention is to provide a new and improved ambidextrous locking clamp system that has a low cost of manufacture with regard to both materials and labor, and which accordingly is then susceptible of low prices of sale to the consuming public, thereby making such ambidextrous locking clamp system economically available to the buying public.

Still another embodiment of the present invention is to provide a new ambidextrous locking clamp system that provides in the apparatuses and methods of the prior art some of the advantages thereof, while simultaneously overcoming some of the disadvantages normally associated therewith.

Lastly another embodiment of the present invention is to provide an ambidextrous locking clamp system for manipulating objects with a tool having removable and interchangeable locking assemblies. This allows the use of the hand operated device by either a right or left handed user.

These together with other embodiments of the invention, along with the various features of novelty that characterize the invention, are pointed out with particularity in the claims annexed to and forming a part of this disclosure. For a better understanding of the invention, its operating advantages and the specific embodiments attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 27 is a front elevational view of an alternate embodiment of the second embodiment of the ambidextrous locking clamp system of FIG. 6.

FIG. 34 is an exploded front elevational view of the alternate embodiment of the fourth embodiment of the present invention.

FIG. 35 is a cross-sectional view taken along the line 35-35 in FIG. 33 of the alternate embodiment of the fourth embodiment of the present invention.

The same reference numerals refer to the same parts throughout the various figures.

DESCRIPTION OF THE PREFERRED EMBODIMENT

Figure 1:
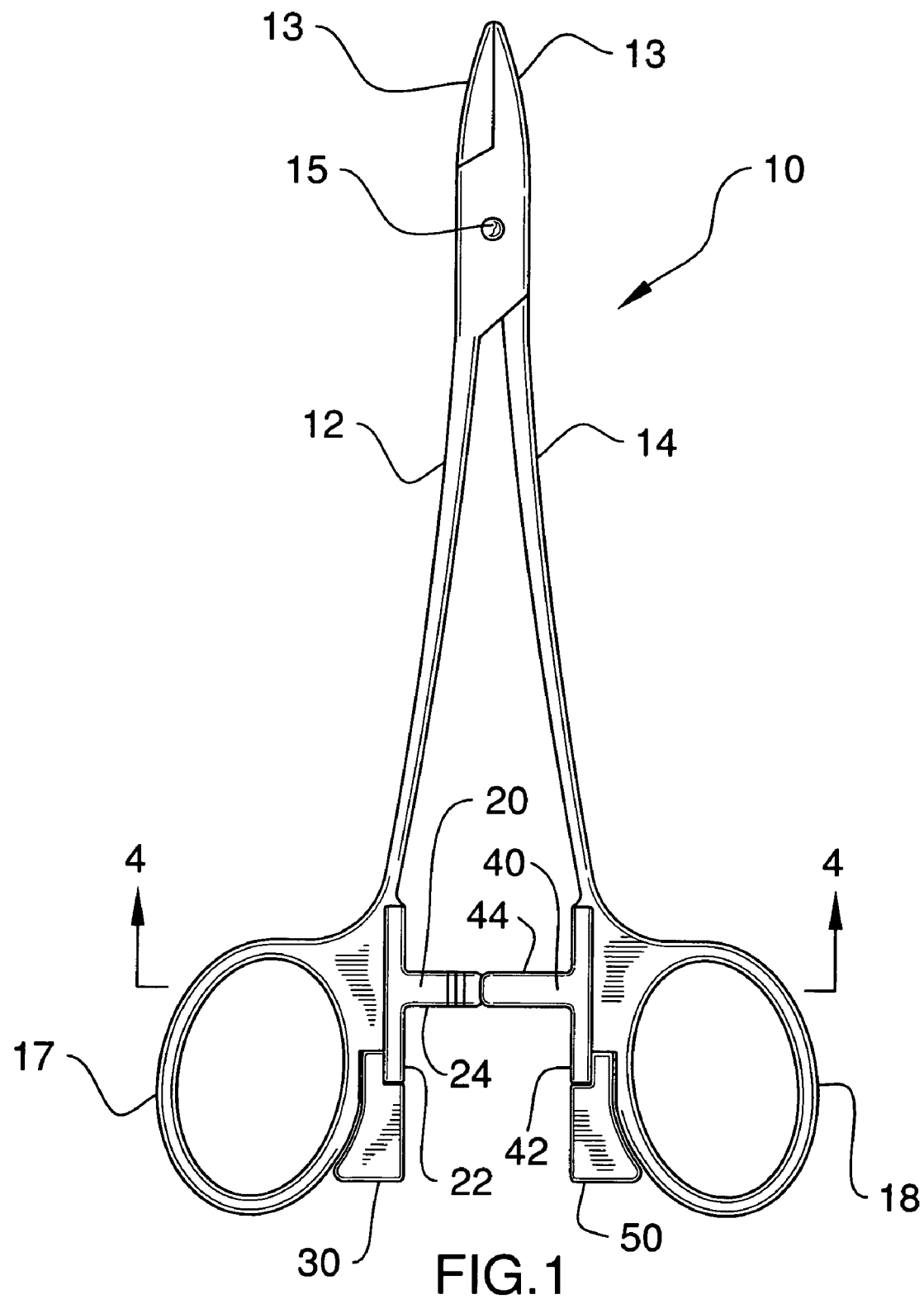
FIG. 1 is a front elevational view of the ambidextrous locking clamp system constructed in accordance with the principles of the present invention.

Referring now to the drawings, and particularly to FIGS. 1-38, a first embodiment of the ambidextrous locking clamp system of the present invention is shown and generally designated by the reference numeral 10.

In FIG. 1, a new and improved ambidextrous locking clamp system 10 of the present invention for allowing the use of a hand operated device by a right or left handed user is illustrated and will be described. More particularly, the ambidextrous locking clamp system 10 has a first elongated member 12 and a second elongated member 14 each having a working head 13, wherein the working heads can be, but not limited to, a gripping jaw or a cutting edge. The second elongated member 14 is connected to the first elongated members 12 via a hinge 15. The first and second elongated members 12 and 14 each have a finger engaging member 17 and 18 located opposite of the working heads 13. A first lever 30 and second lever 50 are pivotally attachable to the finger engaging members 17 and 18, and are orientated so that the levers are facing each other. Additionally, a first latching member 20 is removably attachable to the finger engaging member 17 and a second latching member 40 is removably attachable to the finger engaging member 18. The first and second elongated members 12 and 14 can be made from any suitable material having reflex memory.

Figure 2:
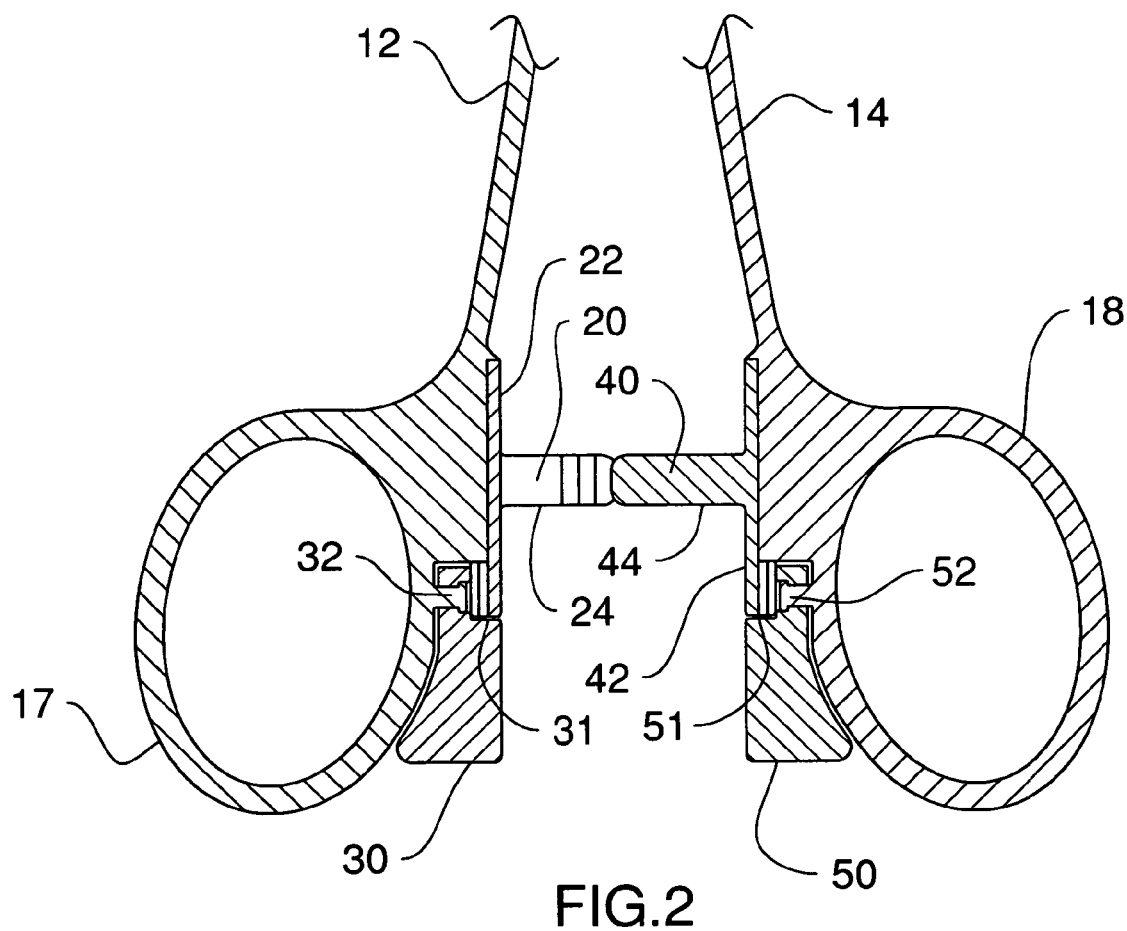
FIG. 2 is an enlarged cross-sectional view of the ambidextrous locking clamp system of the present invention.
Figure 3:
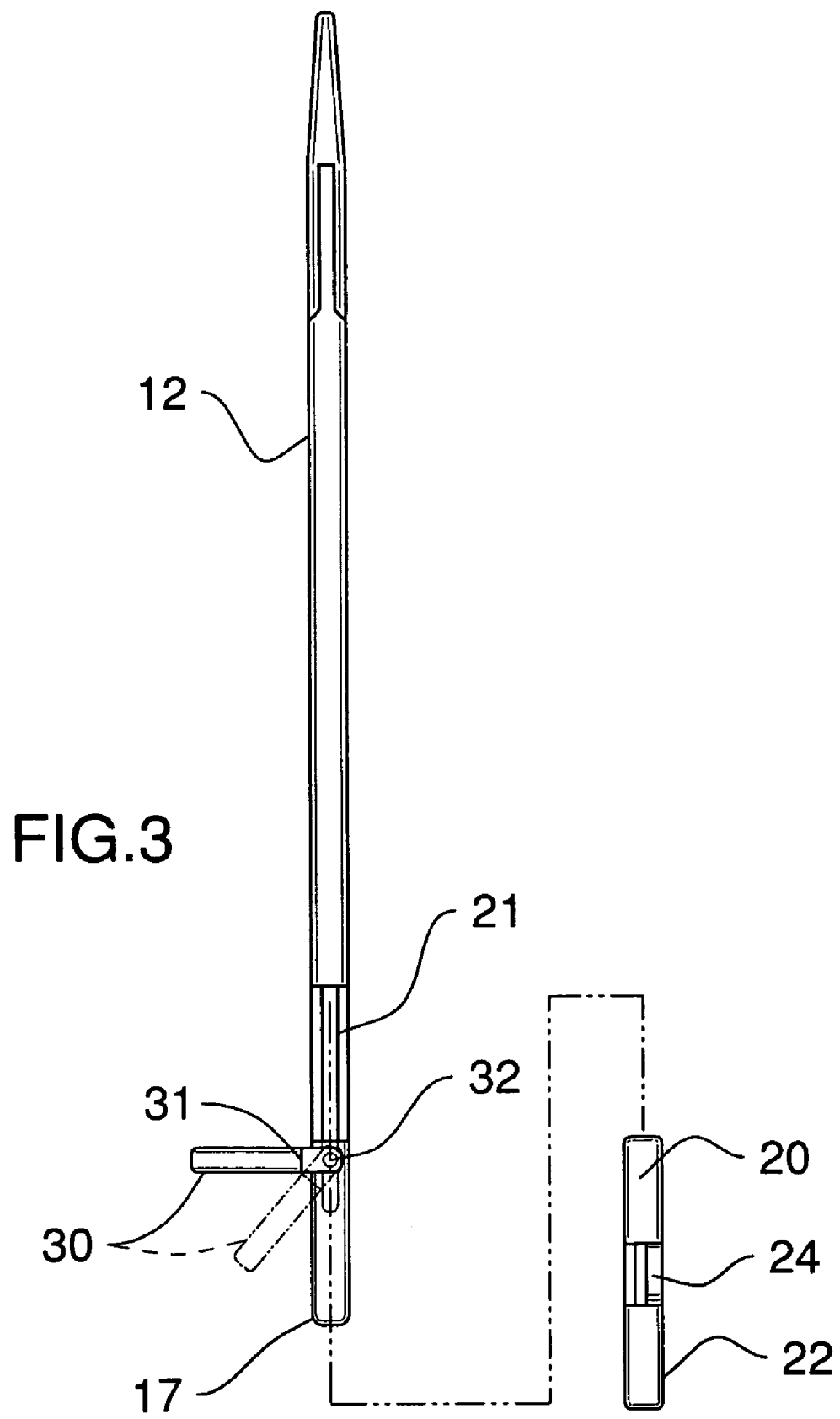
FIG. 3 is an exploded side plane view of the ambidextrous locking clamp system of the present invention.

The levers 30 and 50 have an extended portion for easy operation by the fingers of a user, and are contoured to conform to the shape of the finger engaging members 17 and 18. A pivot pin 32 and 52 extend from the finger engaging members 17 and 18, and through levers 30 and 50, allowing the levers to rotate. The levers 30 and 50 have an extension 31 and 51 for retaining the first and second latching members 20 and 40 on the finger engaging members 17 and 18 when the levers are aligned with the longitudinal axis of the first and second elongated members 12 and 14. When the levers 30 and 50 are rotated to a position perpendicular to the first and second elongated members 12 and 14, the extensions 31 and 51 are able to be moved out of engagement with the first and second latching members 20 and 40, thereby allowing the first and second locking members to slide past the extensions 31 and be removed from finger engaging members 17 and 18. This is best illustrated in FIGS. 2 and 3.

The first and second latching members 20 and 40 each have an elongated base 22 and 42 and a latch arm 24 and 44 extending out from each elongated base. The latch arms 24 and 44 feature a plurality of teeth 26 and 46, which are adapted to join and lock together when engaged. The teeth 26 and 46 are able to disengage when pulled apart by the flexing of the first and second elongated members 12 and 14 when an opposing force is applied to the finger engaging members 17 and 18.

Figure 4:
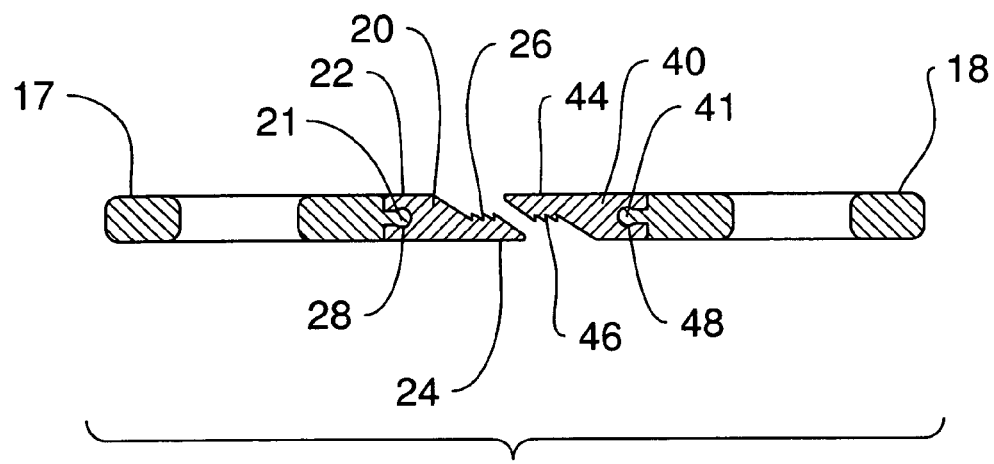
FIG. 4 is a cross-sectional view the locking assembly of the ambidextrous locking clamp system of the present invention.
Figure 5:
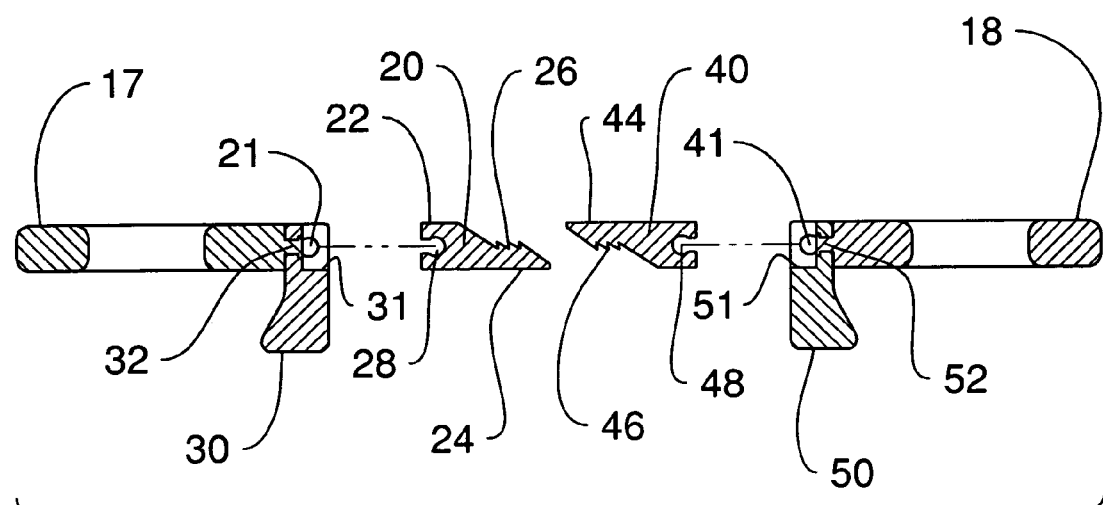
FIG. 5 is an exploded cross-sectional view of the locking assembly of the ambidextrous locking clamp system of the present invention.

The elongated base 22 and 42 of the first and second latching members 20 and 40 each have a channel 28 and 48 running the length of the elongated base. The channels 28 and 48 are adapted to slide on and be retained by a protrusion 21 and 41 extending out from the finger engaging members 17 and 18 and adjacent to the levers 30 and 50. The configuration of the channels 28 and 48 and the protrusions 21 and 41 allow the first and second latching members 20 and 40 to slide over the protrusion, but at the same time not allowing the latching members to be pulled off the protrusions in a direction perpendicular to the sliding motion. FIGS. 4 and 5 best illustrate one possible example of the channel and protrusion configuration.

The first and second latching members 20 and 40 are symmetrical so that they may be removed, inverted and then replaced, thereby changing the orientation of the latching members and allowing a right or left handed user to operate the device 10. Furthermore, other configurations of the first and second latching members 20 and 40 maybe used in place of the above described latching members.

Figure 6:
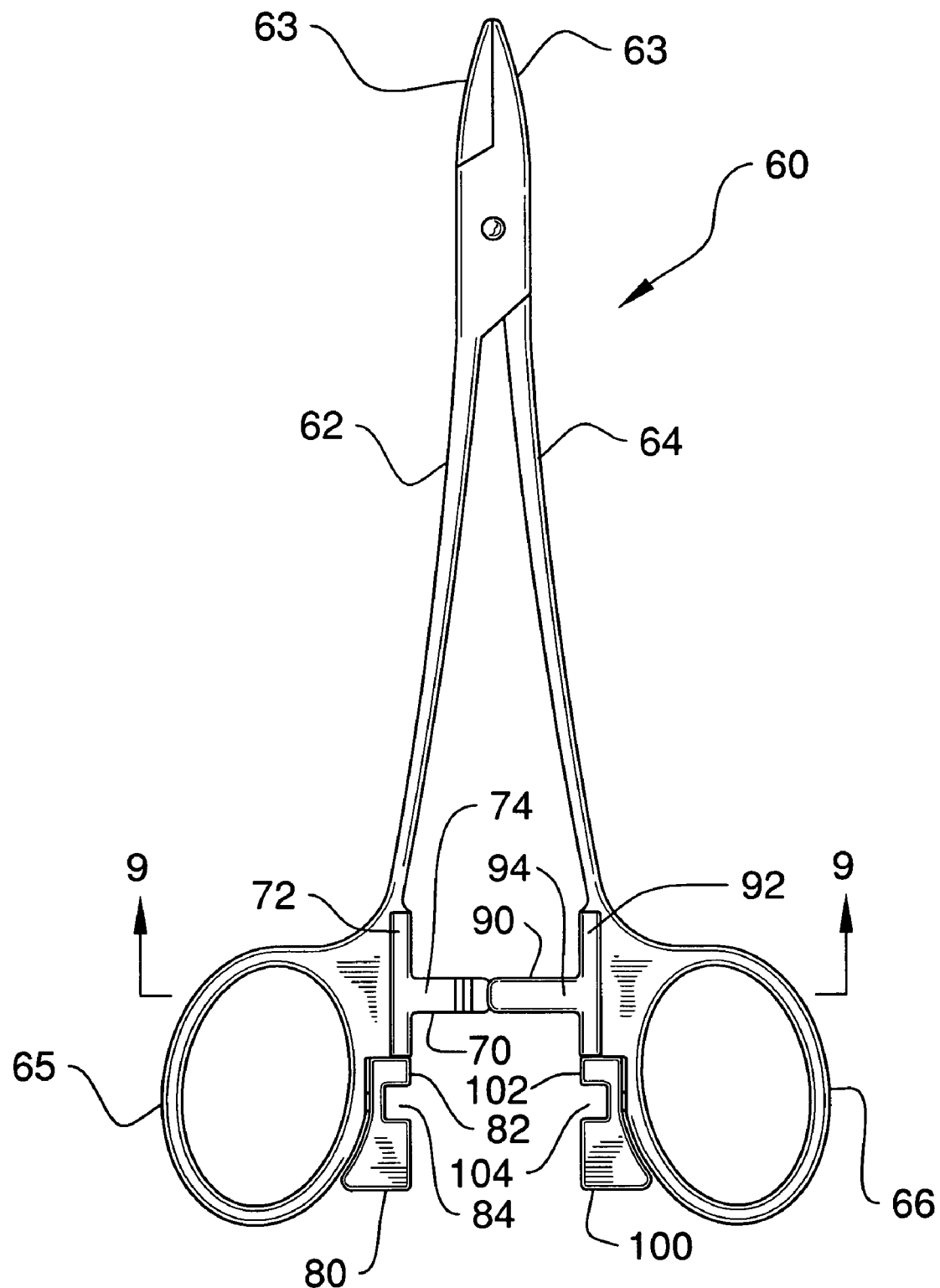
FIG. 6 is a front elevational view of a second alternate embodiment of the ambidextrous locking clamp system of the present invention.

Referring now to FIG. 6, a second alternate embodiment of the ambidextrous locking clamp system of the present invention is shown and generally designated by the reference numeral 60. More particularly, the ambidextrous locking clamp system 60 has a first elongated member 62 and a second elongated member 64 each having a working head 63, wherein the working heads can be, but not limited to, a gripping jaw or a cutting edge. The second elongated member 64 is connected to the first elongate member 62 via a hinge. The first and second elongated members 62 and 64 have a finger engaging member 65 and 66 located opposite of the working heads 63. A first lever 80 and second lever 100 are pivotally attachable to the finger engaging members 65 and 66, and are orientated so that the levers are facing each other. Additionally, a first latching member 70 is removably attachable to the finger engaging member 65 and a second latching member 90 is removably attachable to the finger engaging member 66.

Figure 7:
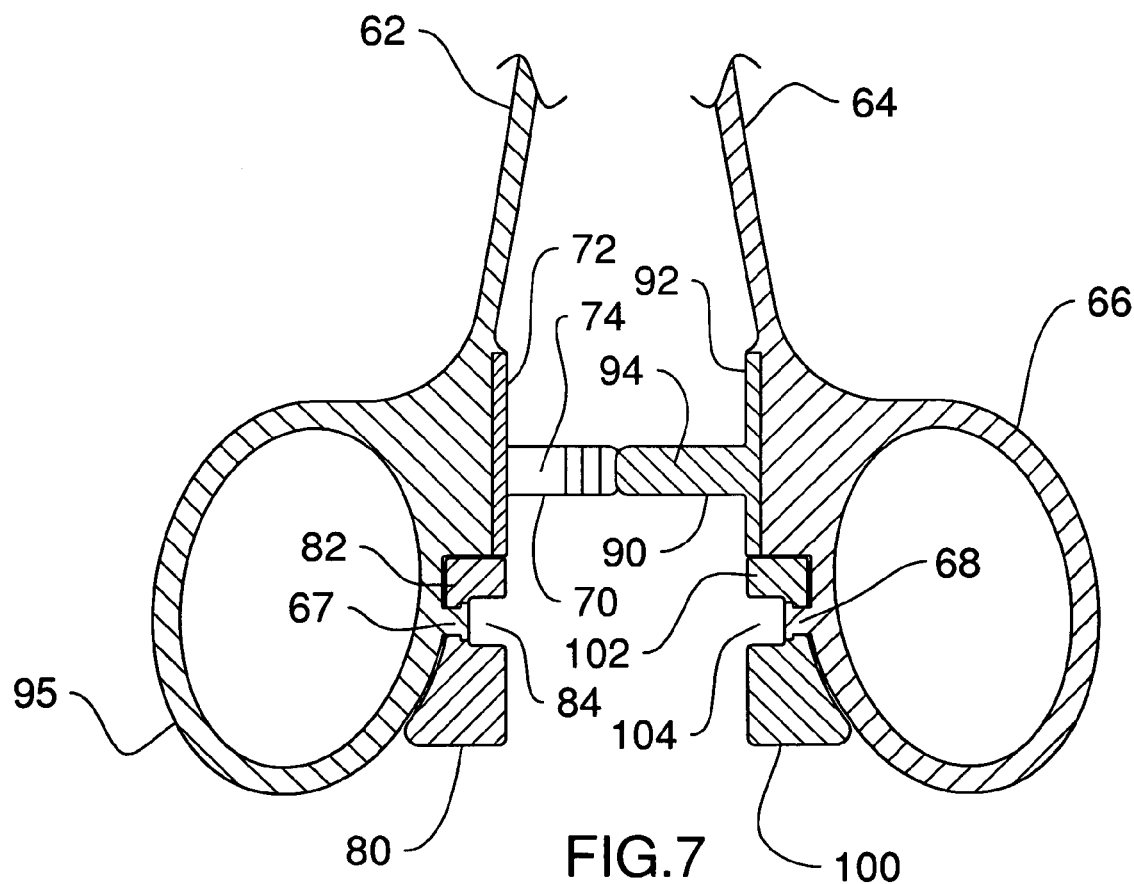
FIG. 7 is an enlarged cross-sectional view of the second alternate embodiment of the present invention.
Figure 8:
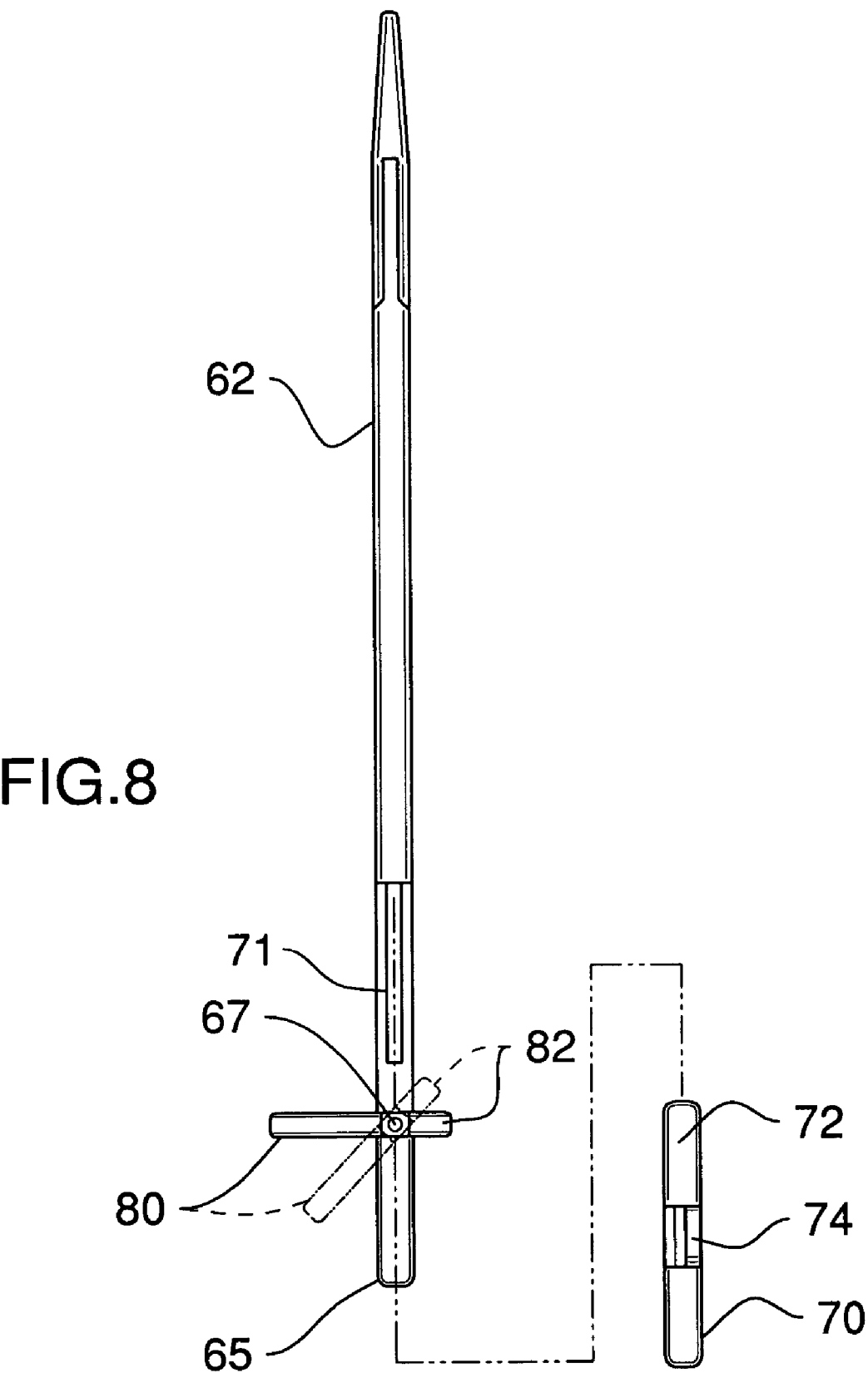
FIG. 8 is an exploded side plane view of the second alternate embodiment of the second alternate embodiment of the present invention.

The levers 80 and 100 have an extended portion for easy operation by the fingers of a user, and are contoured to conform to the shape of the finger engaging members 65 and 66. A pivot pin 67 and 68 extend from the finger engaging members 65 and 66, and through levers 80 and 100, allowing the levers to rotate. The levers 80 and 100 have an extension 82 and 102 for retaining the first and second latching members 70 and 90 on the finger engaging members 65 and 66 when the levers are aligned with the longitudinal axis of the first and second elongated members 62 and 64. A notch 84 and 104 is defined in the levers 80 and 100 for allowing the first and second latching members 70 and 90 to pass therethrough. When the levers 80 and 100 are rotated so they are perpendicular to the first and second elongated members 62 and 64, the extensions 82 and 102 are moved out of engagement with the first and second latching members 70 and 90, and the notches 84 and 104 are exposed to the first and second latching members, thereby allowing the first and second locking members to slide through the notches and removed from finger engaging members 65 and 66. This is best illustrated in FIGS. 7 and 8.

The first and second latching members 70 and 90 each have an elongated base 72 and 92 and a latch arm 74 and 94 extending out from each elongated base. The latch arms 74 and 94 feature a plurality of teeth 76 and 96, which are adapted to join and lock together when engaged. The teeth 76 and 96 are able to disengage when pulled apart by the flexing of the first and second elongated members 62 and 64 when an opposing force is applied to the finger engaging members 65 and 66.

Figure 9:
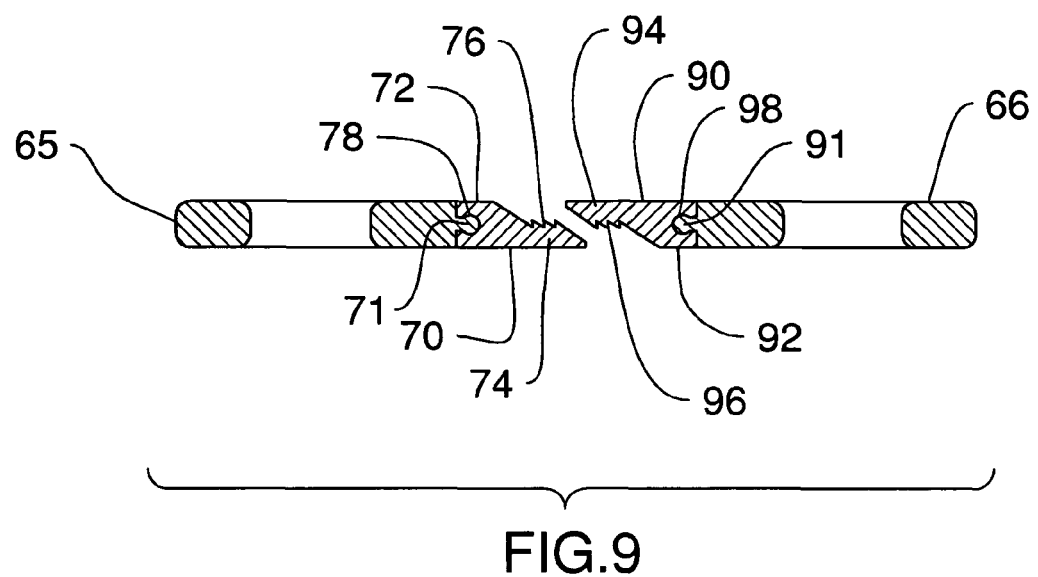
FIG. 9 is a cross-sectional view of the locking assembly of the second alternate embodiment of the present invention.
Figure 10:
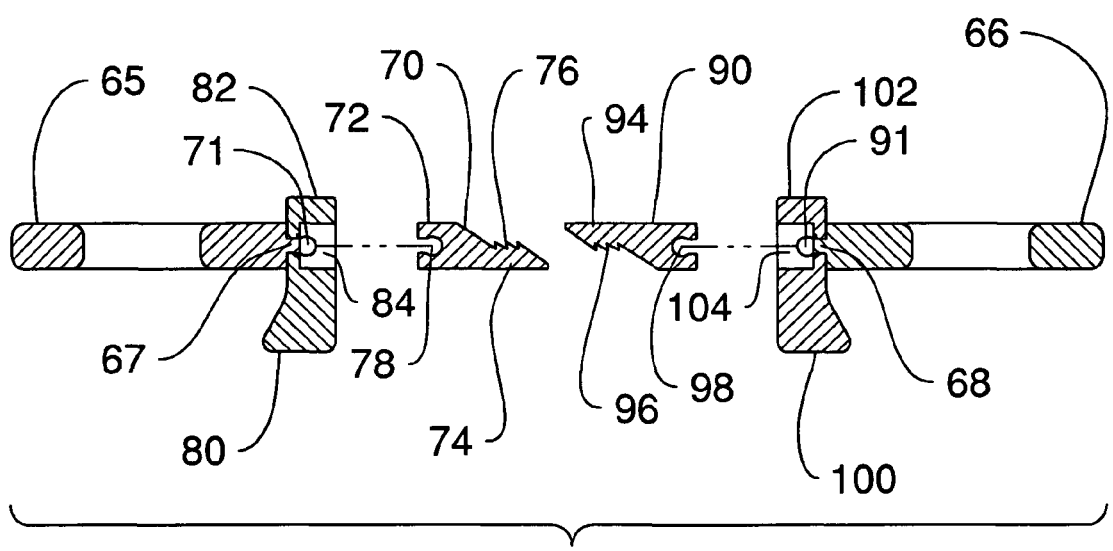
FIG. 10 is an exploded cross-sectional view of the locking assembly of the second alternate embodiment of the present invention.

The elongated base 72 and 92 of the first and second latching members 70 and 90 each have a channel 78 and 98 running the length of the elongated base. The channels 78 and 98 are adapted to slide and be retained by a protrusion 71 and 91 extending out from the finger engaging members 65 and 66 and adjacent to the levers 80 and 100. The configuration of the channels 78 and 98 and the protrusions 71 and 91 allow the first and second latching members 70 and 90 to slide over the protrusion, but at the same time not allowing the latching members to be pulled off the protrusions in a direction perpendicular to the sliding motion. FIGS. 9 and 10 best illustrate one possible example of the channel and protrusion configuration.

The first and second latching members 70 and 90 are symmetrical so that they may be removed, inverted and then replaced, thereby changing the orientation of the latching members and allowing a right or left handed user to operate the device 60. Furthermore, other configurations of the first and second latching members 70 and 90 may be used in place of the above described latching members.

Figure 11:
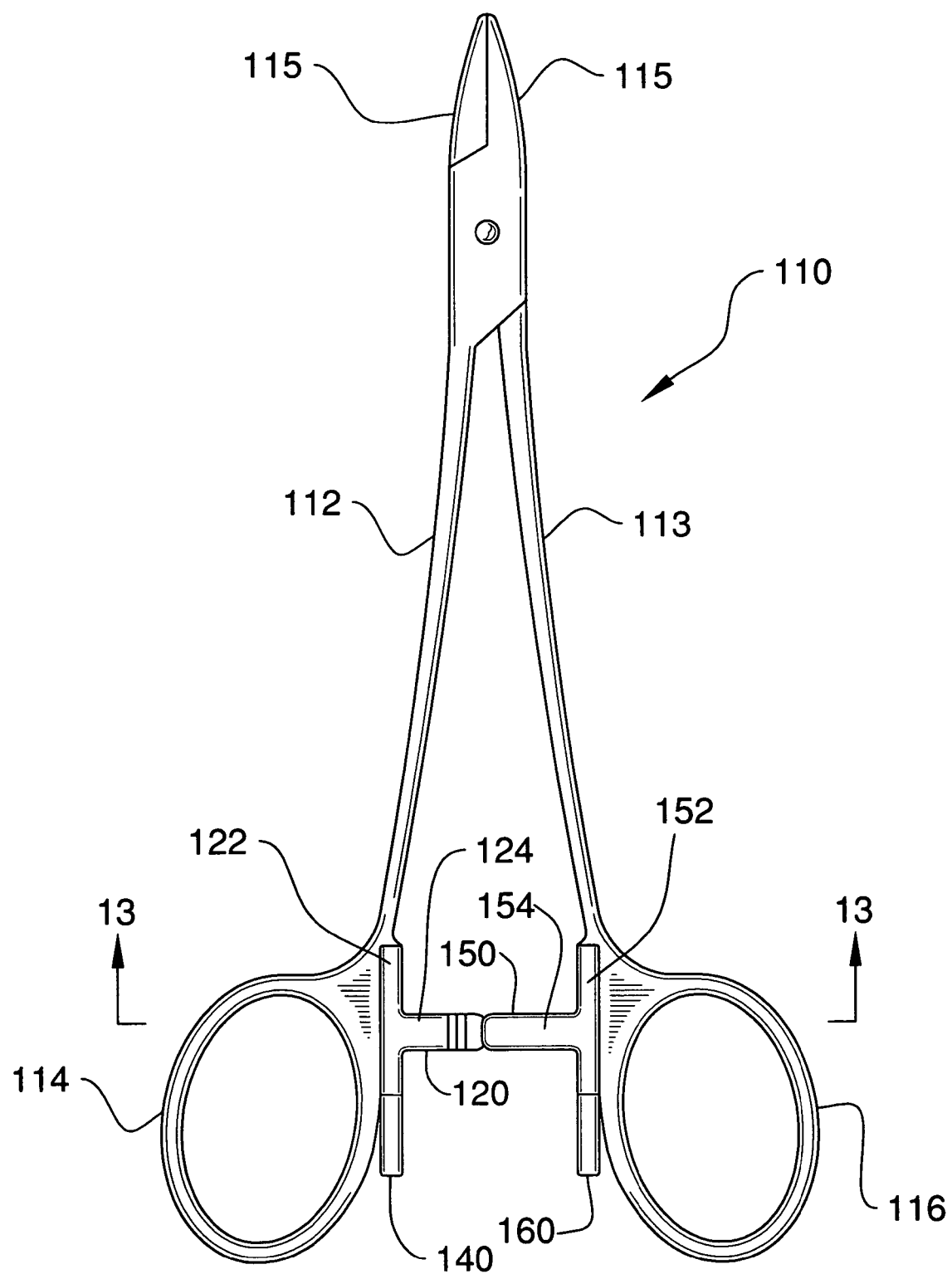
FIG. 11 is a front elevational view of a third alternate embodiment of the ambidextrous locking clamp system of the present invention.

Referring now to FIG. 11, a third alternate embodiment of the ambidextrous locking clamp system of the present invention is shown and generally designated by the reference numeral 110. More particularly, the ambidextrous locking clamp system 110 has a first elongated member 112 and a second elongated member 113 each having a working head 115, wherein the working heads can be, but not limited to, a gripping jaw or a cutting edge. The second elongated member 113 is connected to the first elongate member 112 via a hinge. The first and second elongated members 112 and 113 have a finger engaging member 114 and 116 located opposite of the working heads 115. A first retaining cap 140 and second retaining cap 160 are threadably attachable to the finger engaging members 114 and 116, and are orientated so that the centerline of the caps are aligned with the longitudinal axis of the first and second elongated members 112 and 113. The retaining caps 160 can also be orientated in any alternate position to the first and second elongated members 112 and 113. Additionally, a first latching member 120 is removably attachable to the finger engaging member 114 and a second latching member 150 is removably attachable to the finger engaging member 116.

Figure 12:
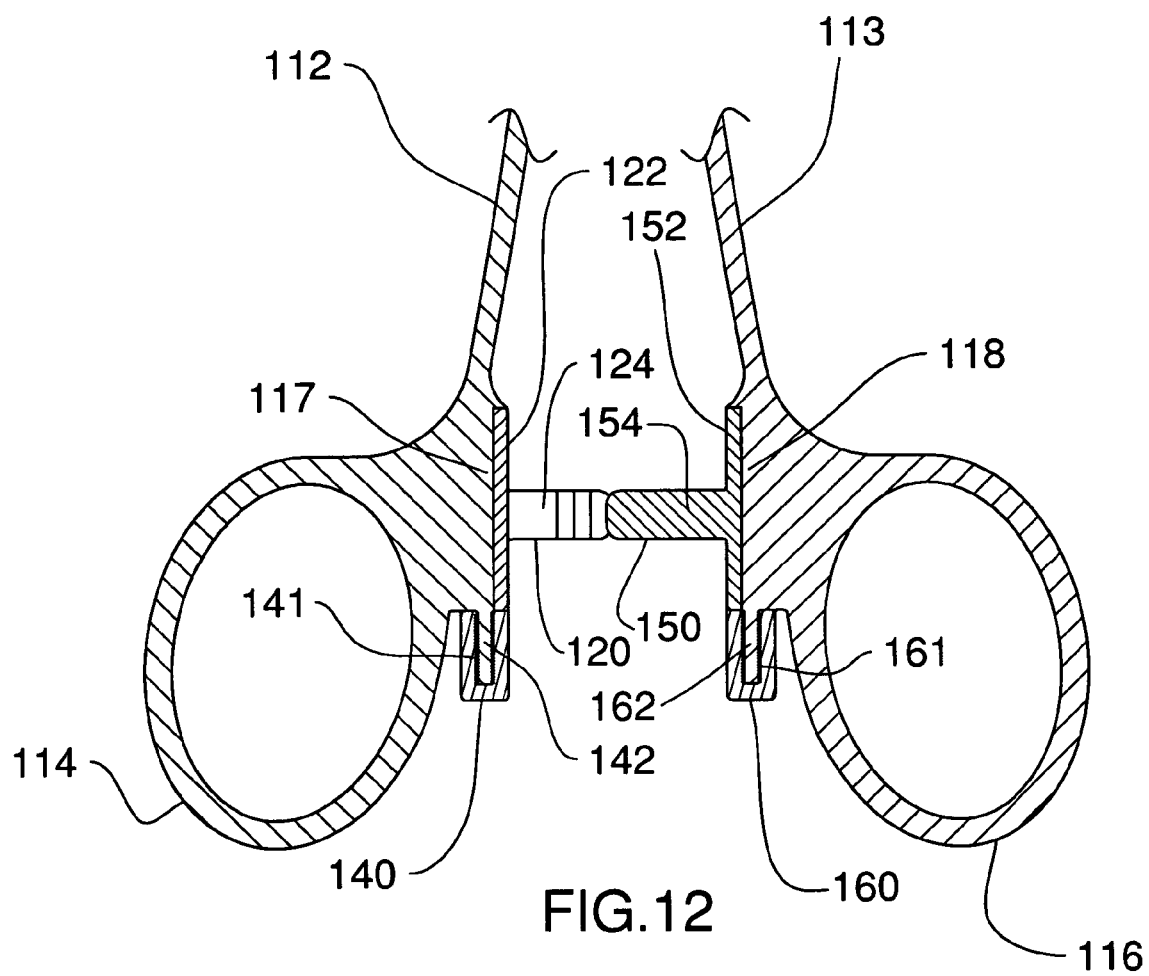
FIG. 12 is an enlarged cross-sectional view of the third alternate embodiment of the present invention.
Figure 14:
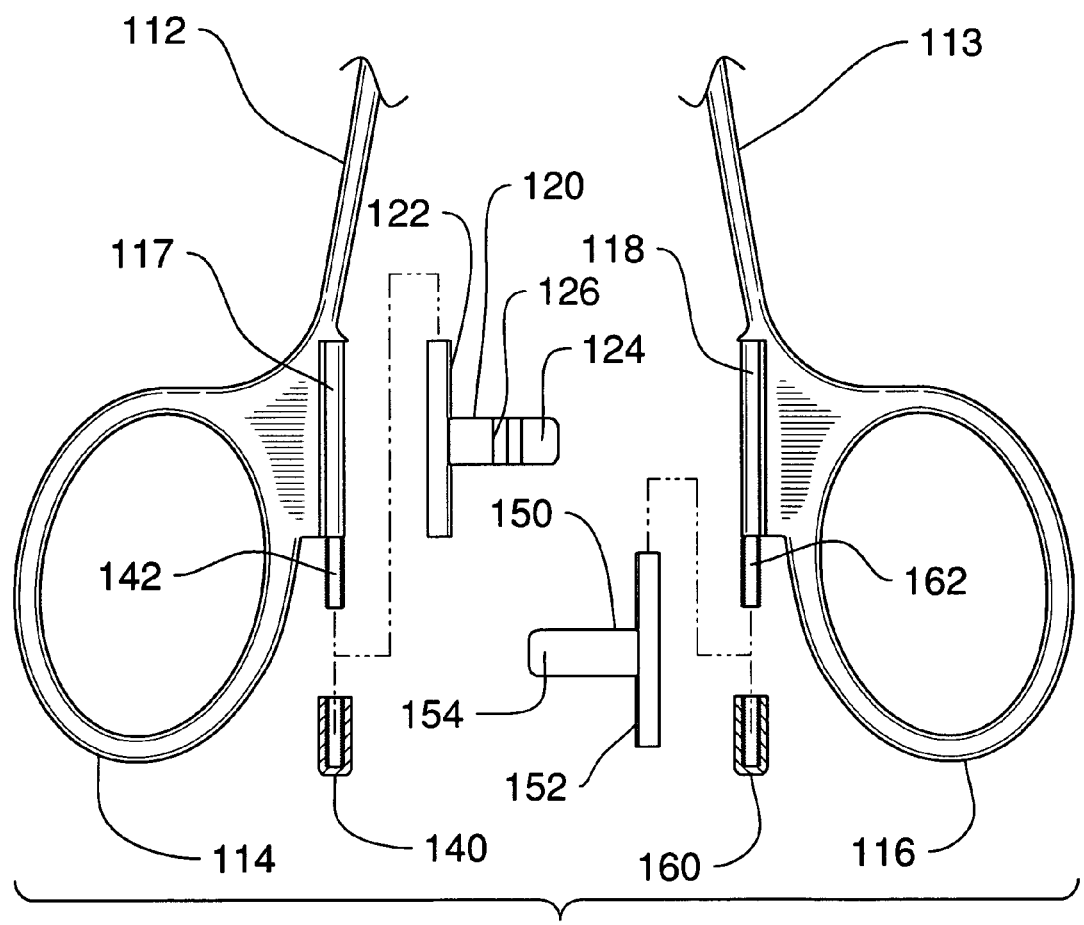
FIG. 14 is an exploded front elevational view of the third alternate embodiment of the present invention.

The retaining caps 140 and 160 have an internal threaded bore 141 and 161. The caps 140 and 160 are adapted to secure the first and second latching members 120 and 150 to the finger engaging members 114 and 116. The caps 140 and 160 are removably attachable to the finger engaging members 114 and 116 by screwing the caps onto a threaded stud 142 and 162 which extends out from a protrusion 117 and 118 of the finger engaging members, and adjacent the first and second latching members 120 and 150. This is best illustrated in FIGS. 12 and 14. The caps 140 and 160 may have a smooth or textured surface, or a fastener driving configuration, such as a screw driver or alien wrench head.

The protrusions 117 and 118 extend out from the finger engaging members 114 and 116, and are adapted to slidably receive the first and second latching members 120 and 150. The threaded studs 142 and 162 extend out from the distal ends of protrusions 117 and 118.

The first and second latching members 120 and 150 each have an elongated base 122 and 152 and a latch arm 124 and 154 extending out from each elongated base. The latch arms 124 and 154 feature a plurality of teeth 126 and 156, which are adapted to join and lock together when engaged. The teeth 126 and 156 are able to disengage when pulled apart by the flexing of the first and second elongated members 112 and 113 when an opposing force is applied to the finger engaging members 114 and 116.

Figure 13:
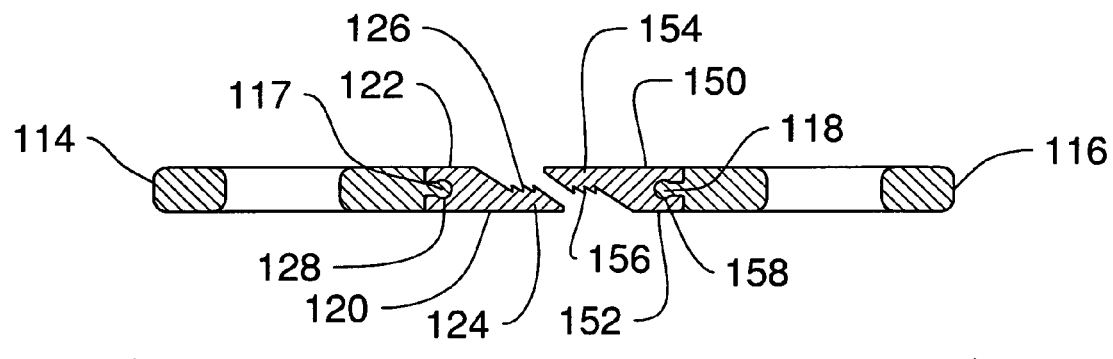
FIG. 13 is a cross-sectional view of the locking assembly of the third alternate embodiment of the present invention.

The elongated base 122 and 152 of the first and second latching members 120 and 150 each have a channel 128 and 158 running the length of the elongated base. The channels 128 and 158 are adapted to slide on and be retained by the protrusions 117 and 118 extending out from the finger engaging members 114 and 116 and adjacent to the threaded studs 142 and 162. The configuration of the channels 128 and 158 and the protrusions 117 and 118 allow the first and second latching members 120 and 150 to slide over the protrusions, but at the same time not allowing the latching members to be pulled off the protrusions in a direction perpendicular to the sliding motion. FIG. 13 best illustrate one possible channel and protrusion configuration.

The first and second latching members 120 and 150 are symmetrical so that they may be removed, inverted and then replaced, thereby changing the orientation of the latching members and allowing a right or left handed user to operate the device 110. Furthermore, other configurations of the first and second latching members 120 and 150 may be used in place of the above described latching members.

Figure 15:
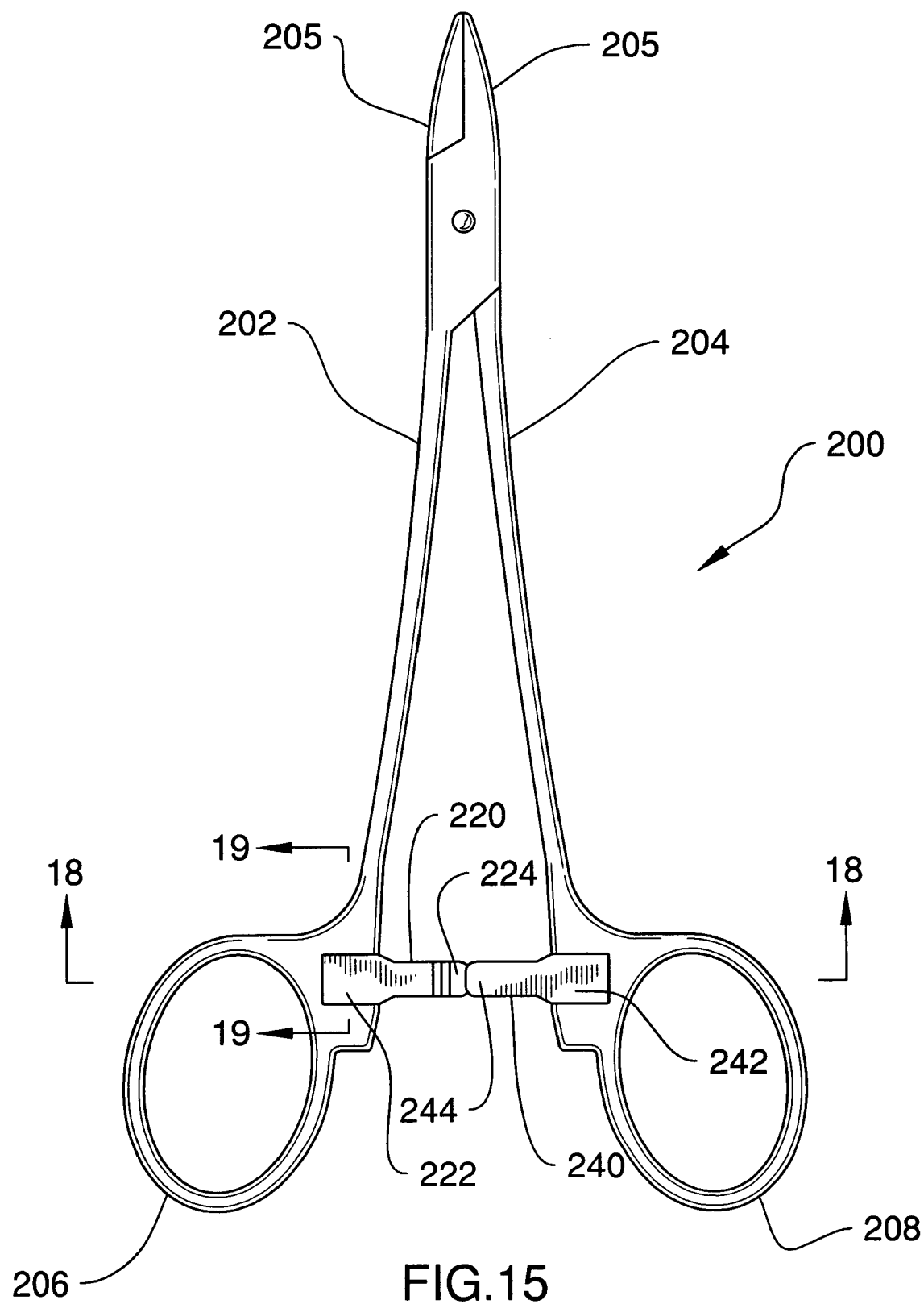
FIG. 15 is a front elevational view of a fourth alternate embodiment of the ambidextrous locking clamp system of the present invention.

Referring now to FIG. 15, a fourth alternate embodiment of the ambidextrous locking clamp system of the present invention is shown and generally designated by the reference numeral 200. More particularly, the ambidextrous locking clamp system 200 has a first elongated member 202 and a second elongated member 204 each having a working head 205, wherein the working heads can be, but not limited to, a gripping jaw or a cutting edge. The second elongated member 204 is connected to the first elongate member 202 via a hinge. The first and second elongated members 202 and 204 each have a finger engaging member 206 and 208 located opposite of the working heads 205. Additionally, a first latching member 220 is removably attachable to the finger engaging member 206 and a second latching member 240 is removably attachable to the finger engaging member 208.

Figure 16:
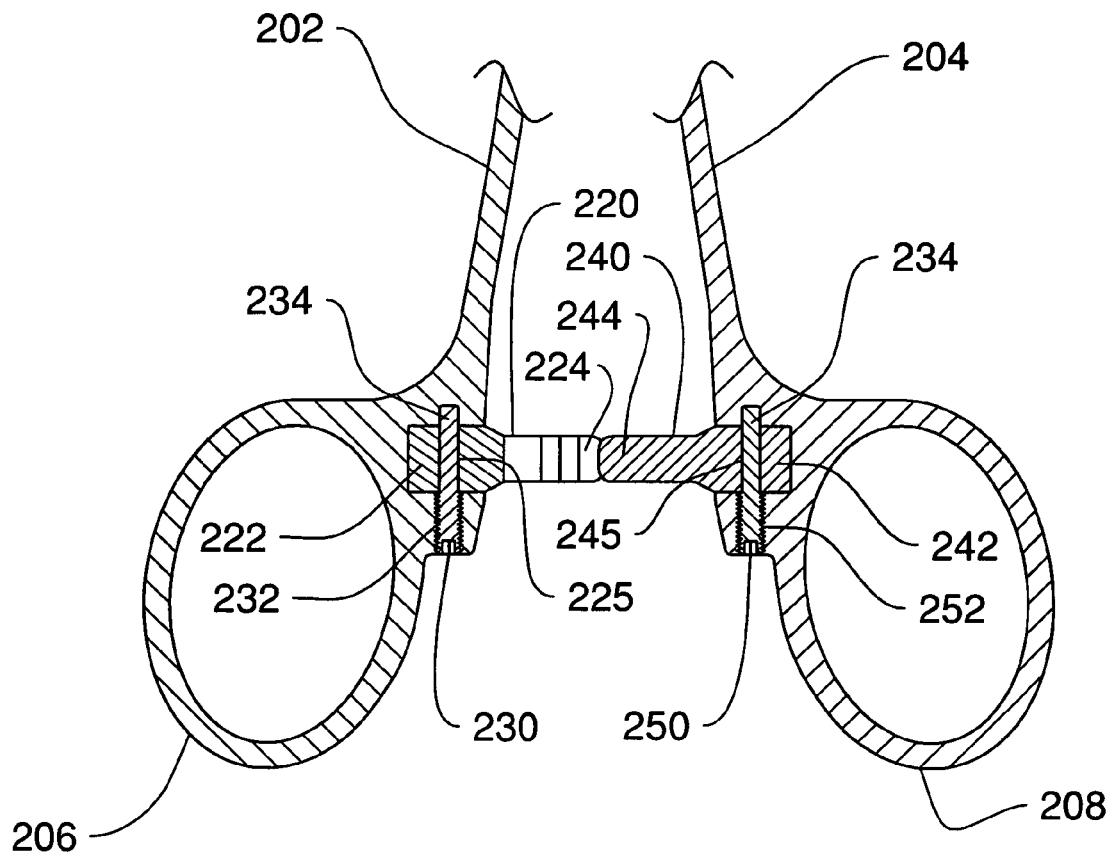
FIG. 16 is an enlarged cross-sectional view of the fourth alternate embodiment of the present invention.

As illustrated in FIG. 16, the first and second latching members 220 and 240 are illustrated in their assembled configuration. The first and second latching members 220 and 240 each have a base 222 and 242 and a latch arm 224 and 244 extending out from each base. The bases 222 and 242 each have an aperture 225 and 245 defined therethrough. A pair of threaded retaining pins 230 and 250 are insertable through a pair of threaded apertures 232 and 252 of the finger engaging members 206 and 208, and through the apertures 225 and 245 of the bases 222 and 242 of the latching members 220 and 240.

Figure 17:
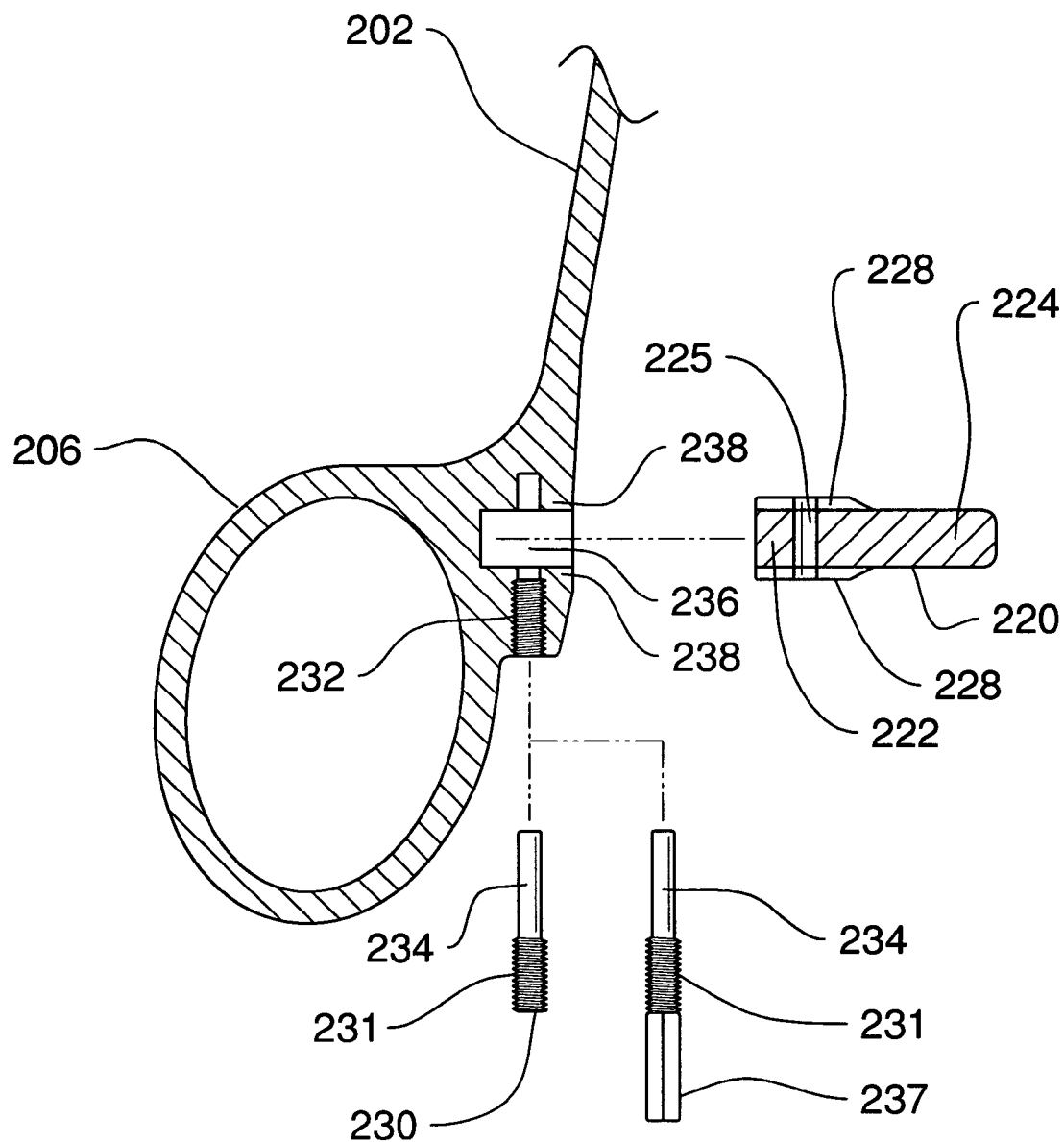
FIG. 17 is an exploded cross-sectional view of the fourth alternate embodiment of the present invention.
Figure 18:
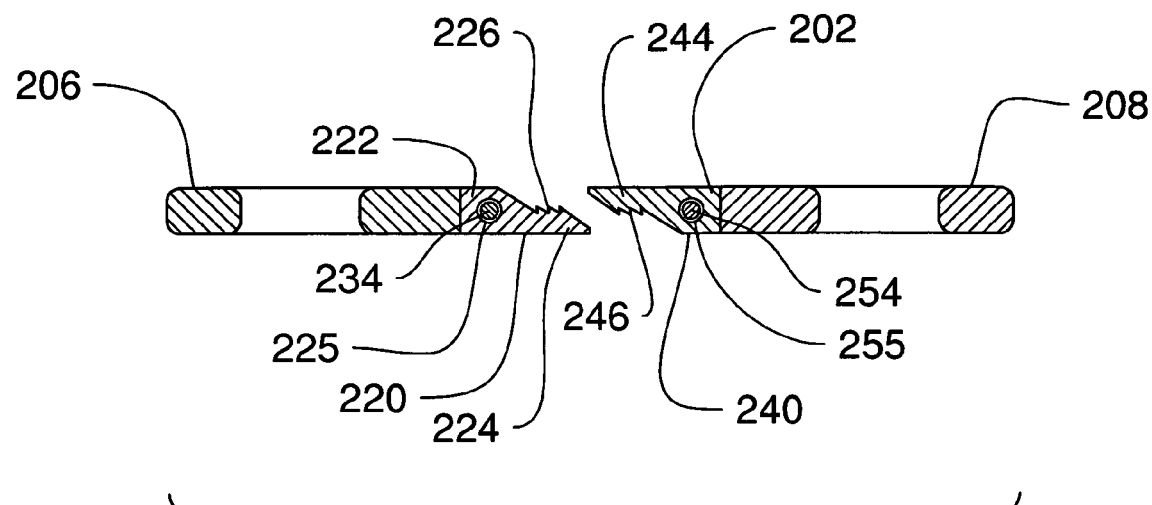
FIG. 18 is a cross-sectional view of the locking assembly of the fourth alternate embodiment of the present invention.
Figure 19:
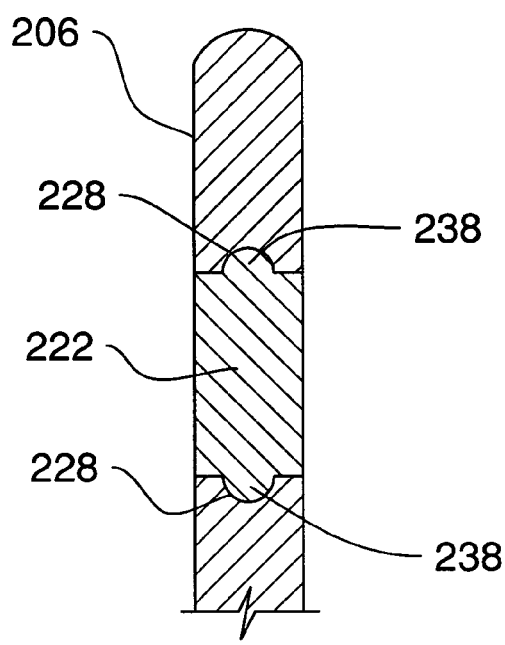
FIG. 19 is a cross-sectional view of the locking assembly of the fourth alternate embodiment of the present invention.

A more detailed illustration of the first latch member 220 and finger engaging member 206 assembly is shown in FIG. 17, whereby the second latch member 240 and finger engaging member 208 assembly is a mirror image thereof and therefore not shown. The threaded retaining pins 230 and 237 have a threaded end 231 featuring a driving head or detent, and a non-threaded section 234. The non-threaded section 234 is adapted to be received through a threaded aperture 232 and 252 of the finger engaging members 206 and 208, and through the apertures 225 and 245 of the latching members 220 and 240. The threaded end 231 engages the threaded apertures 232 and 252 to secure the retaining pins 230 and 250 in the finger engaging members 206 and 208, thereby securing the latching members 220 and 240 in a notch 236 located in each of the finger engaging members. The latching members 220 and 240 are slidably insertable into notches 236 so that the bases 222 and 242 rest in the notches. The bases 222 and 242 of the latching members 220 and 240 have a pair of channels 228 running the length of the base parallel with the longitudinal axis of the latch arms 224 and 244. As best illustrated in FIGS. 17 and 18, the channels 228 are adapted to receive a set of protrusions 238 which extend into the notch 236. The channel 228 and protrusion 238 connection is configured to retain the latching members 220 and 240 in the notch 236 and flush with the outer surface of the finger engaging members 206 and 208. Additionally, the channel 228 and protrusion 238 connection prevents the latching members 220 and 240 from rotating out of alignment with the notch 236. FIG. 18 best illustrate one possible channel and protrusion configuration.

The latch arms 224 and 244 feature a plurality of teeth 226 and 246, which are adapted to join and lock together when engaged. The teeth 226 and 246 are able to disengage when pulled apart by the flexing of the first and second elongated members 202 and 204 when an opposing force is applied to the finger engaging members 206 and 208. The first and second latching members 220 and 240 are symmetrical so that they may be removed, inverted and then replaced, thereby changing the orientation of the latching members and allowing a right or left handed user to operate the device 200. Furthermore, other configurations of the first and second latching members 220 and 240 may be used in place of the above described latching members.

Figure 20:
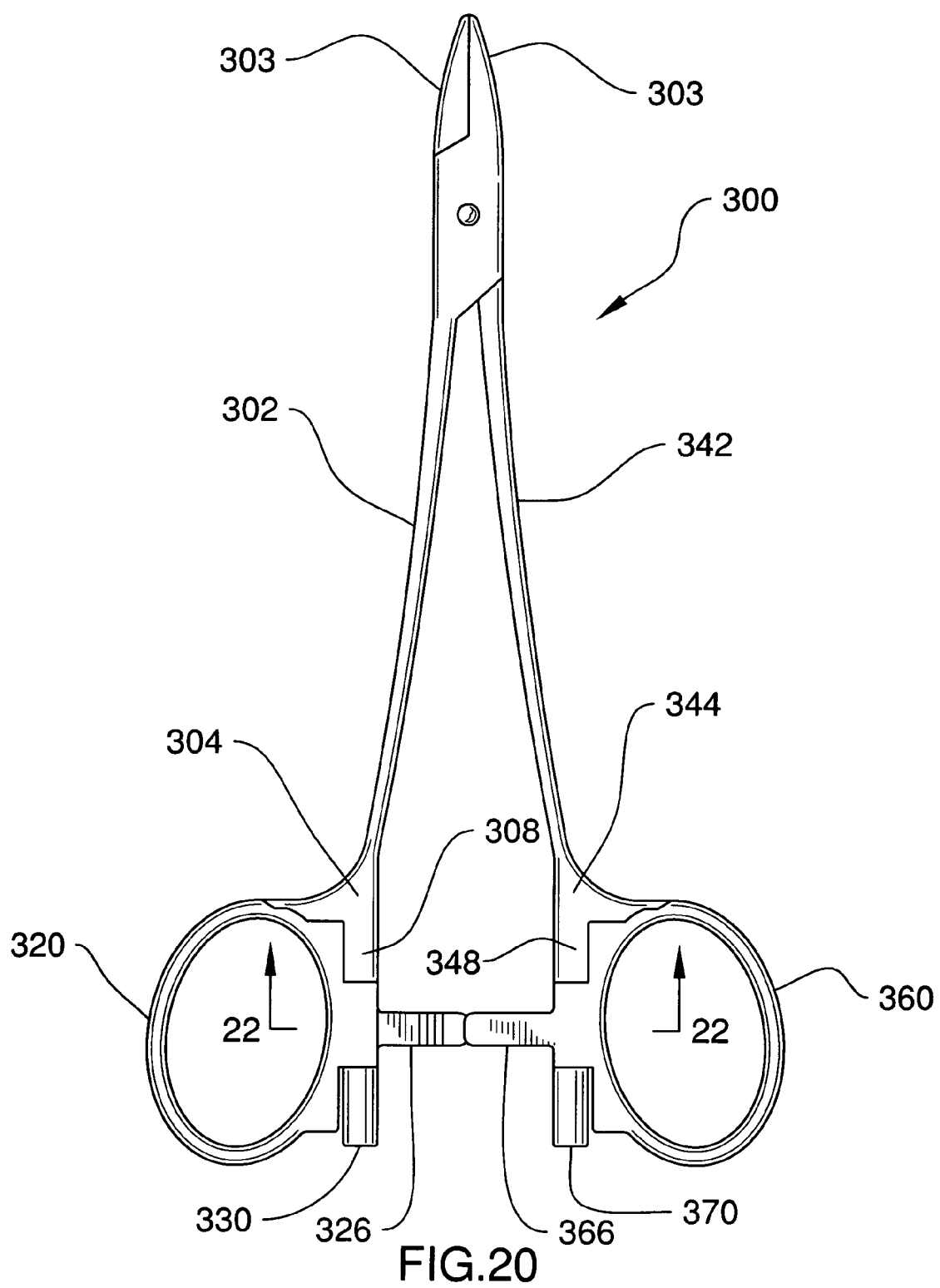
FIG. 20 is a front elevational view of a fifth alternate embodiment of the ambidextrous locking clamp system of the present invention.
Figure 21:
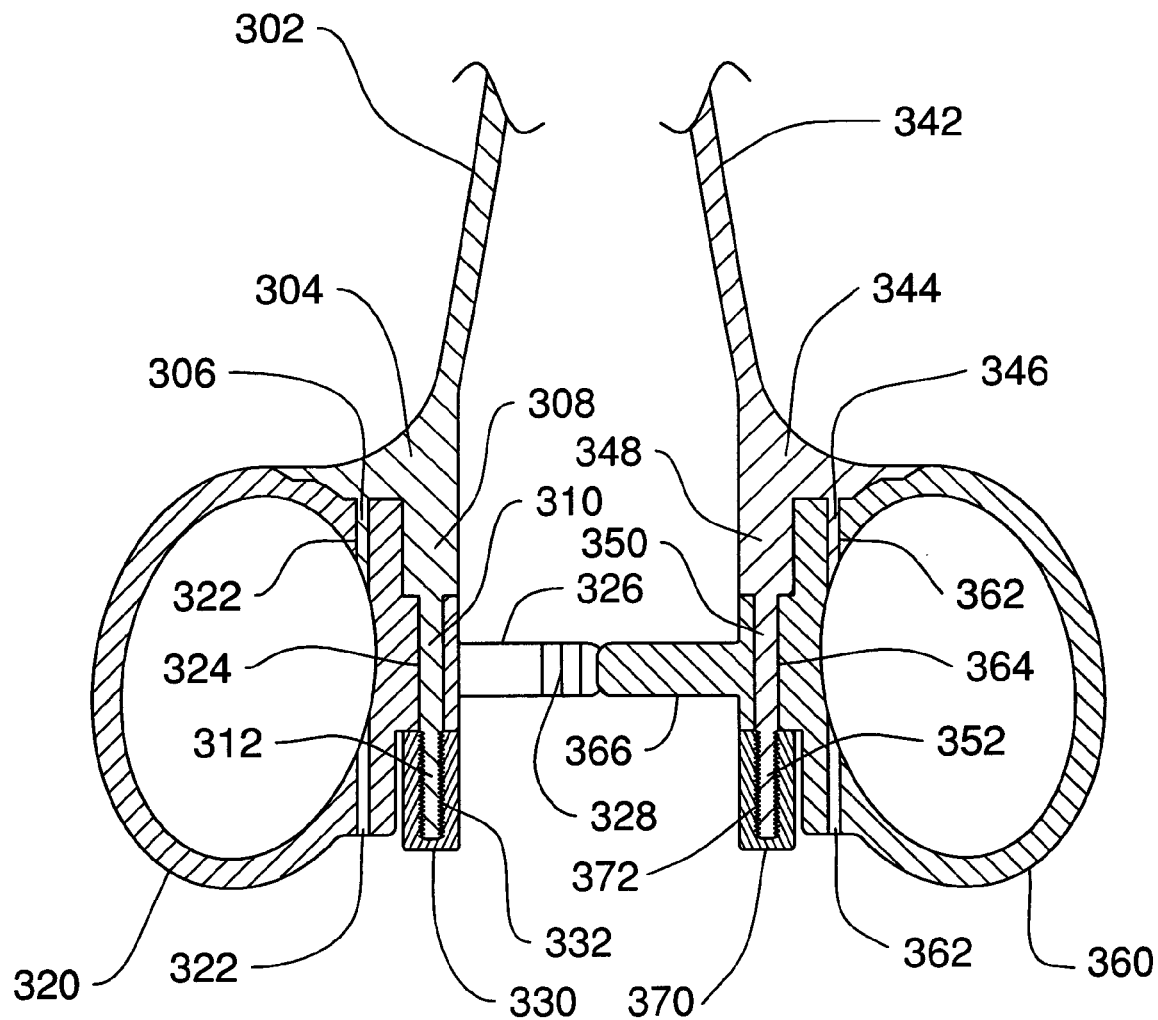
FIG. 21 is an enlarged cross-sectional view of the fifth alternate embodiment of the present invention.
Figure 22:
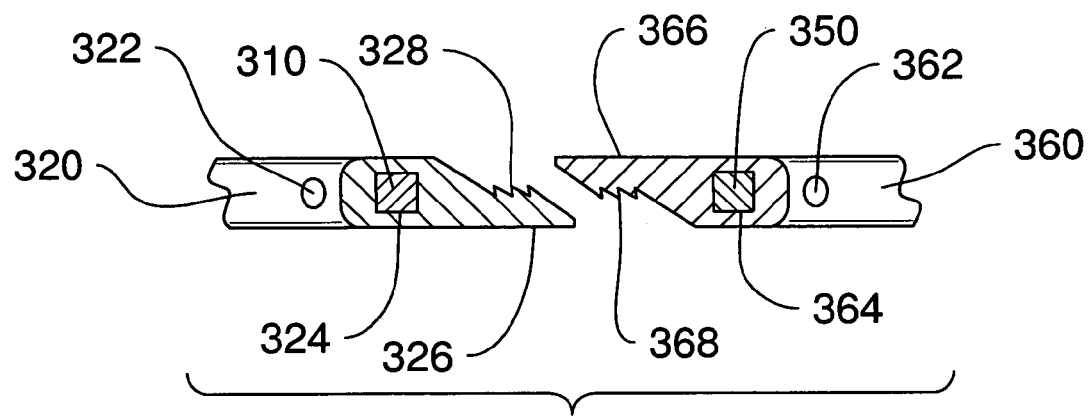
FIG. 22 is a cross-sectional view of the locking assembly of the fifth alternate embodiment of the ambidextrous locking clamp system of the present invention.

Referring now to FIG. 20, a fifth alternate embodiment of the ambidextrous locking clamp system of the present invention is shown and generally designated by the reference numeral 300. More particularly, the ambidextrous locking clamp system 300 has a first elongated member 302 and a second elongated member 342 each having a working head 303, wherein the working heads can be, but not limited to, a gripping jaw or a cutting edge. The second elongated member 342 is connected to the first elongate member 302 via a hinge. The first and second elongated members 302 and 342 each have a removable finger engaging member 320 and 360 located opposite of the working heads 303. Each removable finger engaging member 320 and 360 has a latching arm 326 and 346 extending out and towards each other. A first retaining cap 330 and second retaining cap 370 are threadably attachable to the first and second elongated members 302 and 342, and are orientated so that the centerline of the caps are aligned with the longitudinal axis of the first and second elongated members. The retaining caps 330 and 370 can also be orientated in any alternate position to the first and second elongated members 302 and 342. The first and second retaining caps 330 and 370 are adapted to secure the finger engaging members 320 and 360 to the first and second elongated members 302 and 342.

The first and second elongated members 302 and 342 each have a finger engaging member receiving assembly 304 and 344. The finger engaging member receiving assemblies 304 and 344 each have a protrusion 306 and 346, and a retaining rod 308 and 348. The retaining rods 308 and 348 include a stem 310 and 350 extending out therefrom, each with a threaded end 312 and 352. The first and second retaining caps 330 and 370 have internally threaded bores 332 and 372 able to be threaded on to the treaded ends 312 and 352 of the stems 310 and 350.

Figure 23:
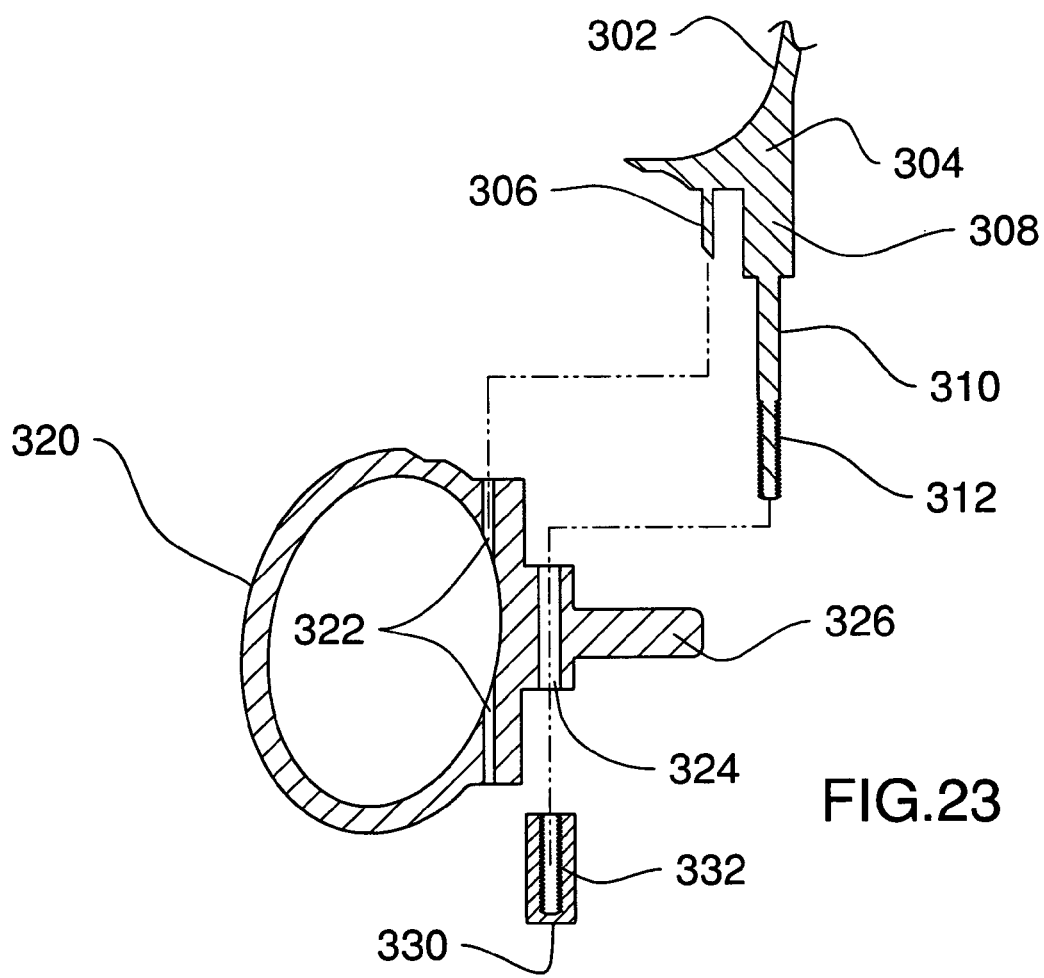
FIG. 23 is an exploded cross-sectional view of the fifth alternate embodiment of the present invention.

The finger engaging members 320 and 360 each have a bore 322 and 362 adapted to receive the protrusions 306 and 346 of the finger engaging member receiving assemblies 304 and 344. The finger engaging members 320 and 360 also have an aperture 324 and 364 running parallel with the bores 322 and 344, which correspond to the configuration of the stems 310 and 350, and to the retaining rods 308 and 348. The finger engaging members 320 and 360 are positioned on to the protrusions 306 and 346, and to the retaining rods 308 and 348, and are then secured to the finger engaging member receiving assemblies 304 and 344 by securing the retaining caps 330 and 370 on to the threaded ends 312 and 352 of stems 310 and 350, as best illustrated in FIG. 23.

The latching arms 326 and 366 each have a plurality of teeth 328 and 368, which are adapted to join and lock together when engaged. The teeth 328 and 368 are able to disengage when pulled apart by the flexing of the first and second elongated members 302 and 342 when an opposing force is applied to the finger engaging members 320 and 360. The first and second finger engaging members 320 and 360 are symmetrical so that they may be removed, inverted and then replaced, thereby changing the orientation of the latching members and allowing a right or left handed user to operate the device 300. Furthermore, other configurations of the first and second finger engaging members 320 and 360 may be used in place of the above described latching members.

Figure 24:
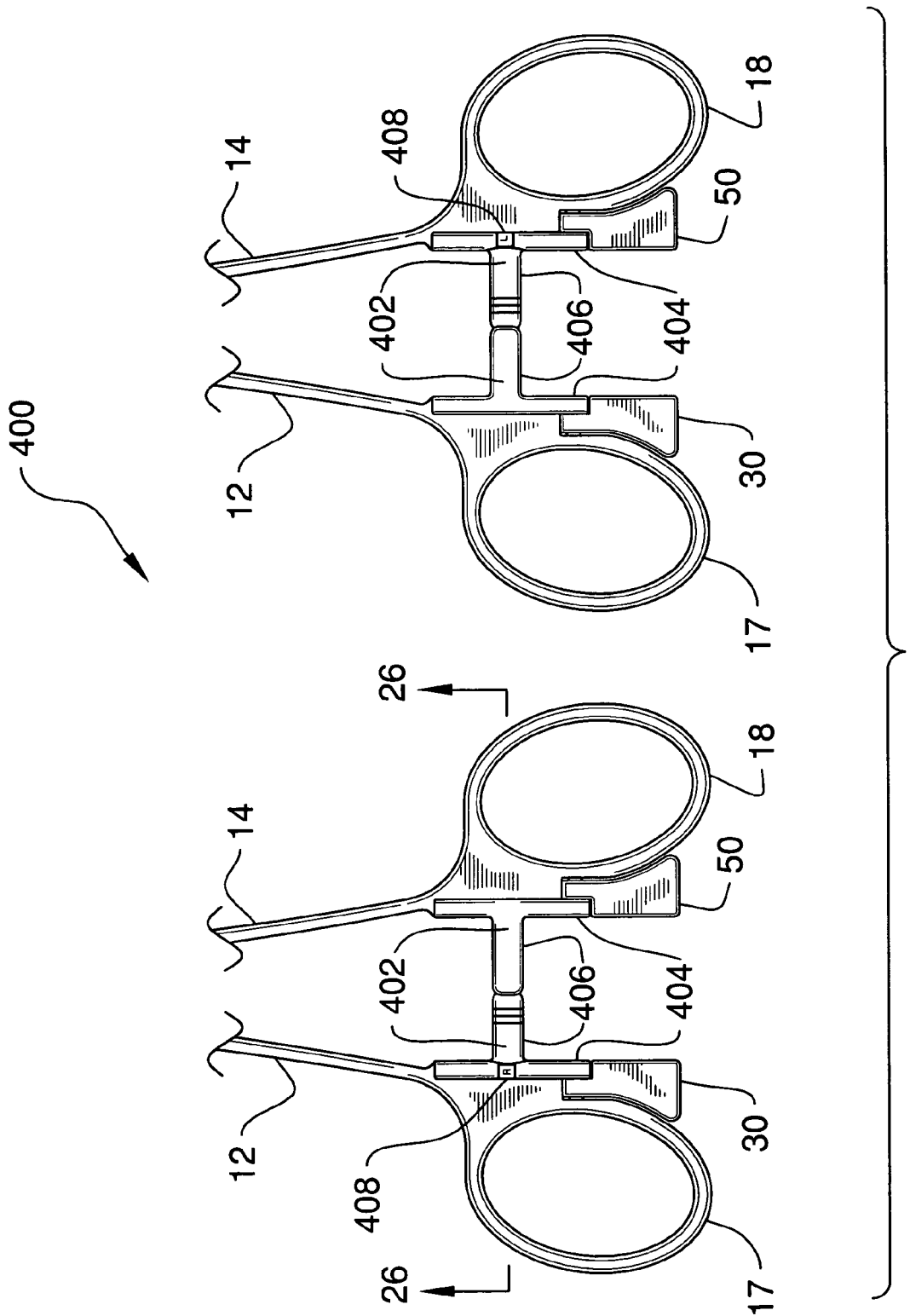
FIG. 24 is a front elevational view of an alternate embodiment of the ambidextrous locking clamp system of FIG. 1.

Referring now to FIG. 24 which illustrates an alternate embodiment 400 of the present invention shown in FIG. 1. This alternate embodiment has a first elongated member 12 hingedly connected to a second elongated member 14. Both the first and second elongated members 12 and 14 each have a working head 13 and a finger engaging member 17 and 18 located opposite of the working head (not shown). A first lever 30 and second lever 50 are pivotally attachable to the finger engaging members 17 and 18, and are orientated-so that the levers are facing each other. Additionally, latching members 402 are removably attachable to the finger engaging members 17 and 18. Each latching member 402 has a notch 408 for viewing an indicator located on the finger engaging members 17 and 18. The first and second elongated members 12 and 14 can be made from any suitable material having reflex memory.

Figure 25:
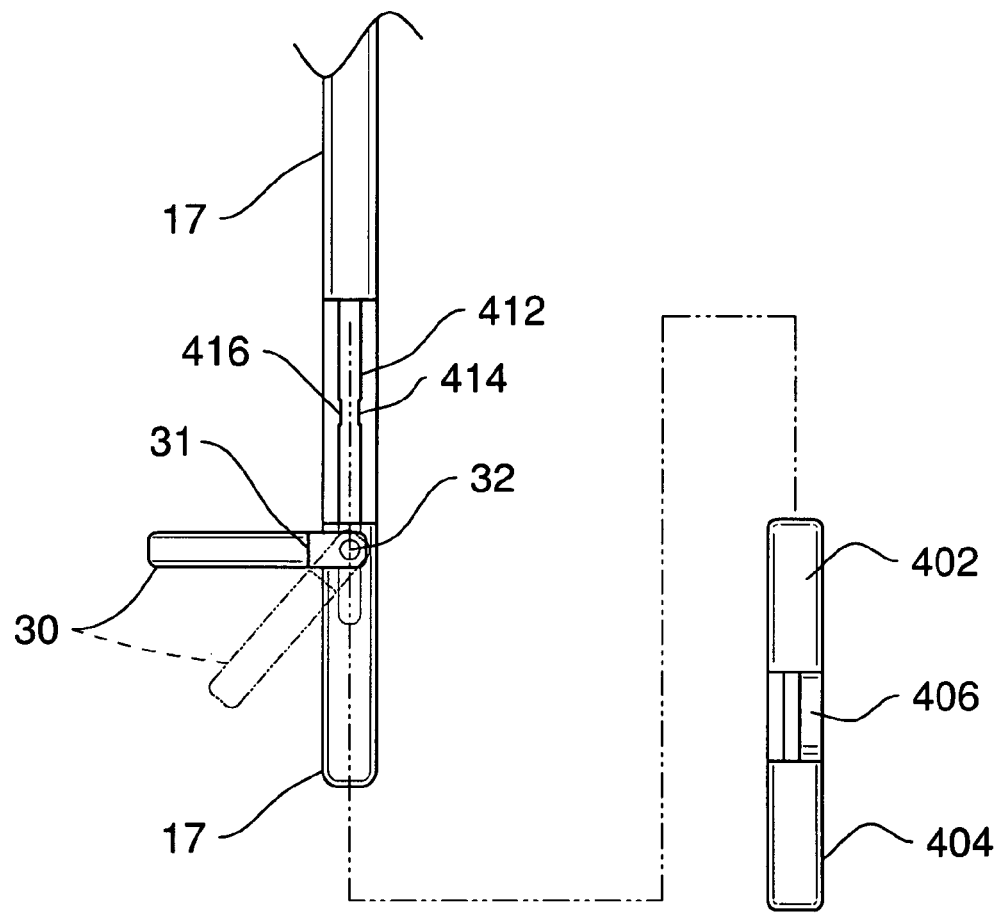
FIG. 25 is an exploded side elevational view of the locking assembly of the alternate embodiment of the present invention.

The levers 30 and 50 have an extended portion for easy operation by the fingers of a user, and are contoured to conform to the shape of the finger engaging members 17 and. 18. A pivot pin 32 extends from the finger engaging members 17 and 18, and through levers 30 and 50, allowing the levers to rotate. The levers 30 and 50 have an extension 31 for retaining the latching members 402 on the finger engaging members 17 and 18 when the levers are aligned with the longitudinal axis of the first and second elongated members 12 and 14, as best illustrated in FIG. 25. When the levers 30 and 50 are rotated to a position perpendicular to the first and second elongated members 12 and 14, the extensions 31 are able to be moved out of engagement with the latching members 402, thereby allowing the latching members to slide past the extensions 31 and be removed from finger engaging members 17 and 18.

The latching members 402 each have an elongated base 404 and a latch arm 406 extending out from each elongated base. The latch arms 406 feature a plurality of teeth 410, which are adapted to join and lock together when engaged. The teeth 410 are able to disengage when pulled apart by the flexing of the first and second elongated members 12 and 14 when an opposing force is applied to the finger engaging members 17 and 18.

The elongated base 404 of the latching members 402 each have a channel 409 running the length of the elongated base. The channels 409 are adapted to slide on and be retained by protrusions 412 extending out from the finger engaging members 17 and 18 and adjacent to the levers 30 and 50. The protrusions 412 each have an indicator 414 and 416 located on opposite sides of the protrusion. The indicators 414 and 416 have a marking or indicia thereon to indicate a right or left hand use. The marking or indicia can be, but not limited to, the letter "R" and "L". The arrangement of indicators 414 and 416 are opposite for finger engaging members 17 and 18, so that not similar indicators are facing the user. This allows the user to view, from either side, through the notch 408 what orientation the ambidextrous locking clamp 400 is set for, as best shown in FIG. 24 which illustrates a right and left handed orientation.

Figure 26:
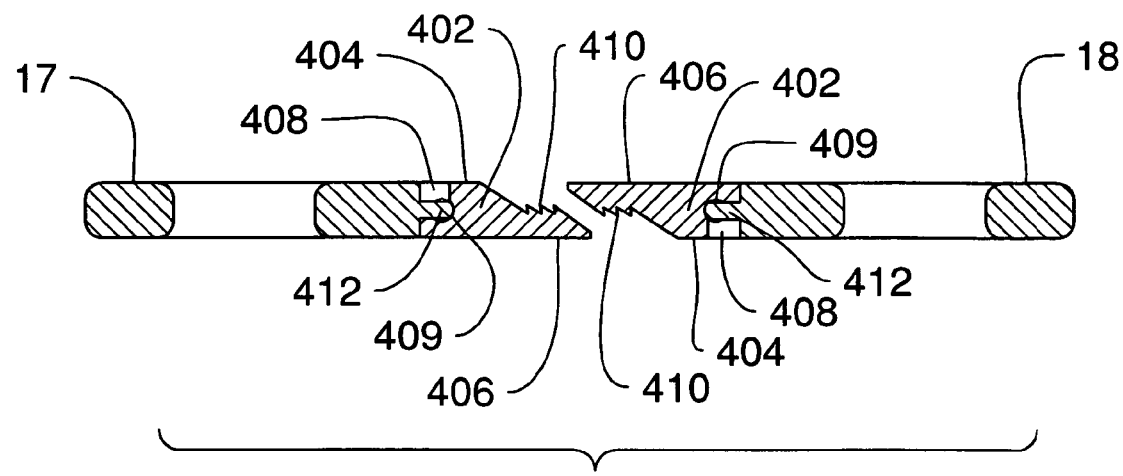
FIG. 26 is a cross-sectional view taken along the line 26-26 in FIG. 24 of the alternate embodiment of the present invention.

The notch 408 is located on the elongated base 404 on the same side as the teeth 410. The notch 408 extends into the channel 409. When the latching members 402 are positioned on the protrusions 412, the notch 408 is located over either the indicator 414 or 416, depending on what orientation the latching members are set at for use either by a left or right handed user. The configuration of the channel 409 and the protrusions 412 allow the latching members 402 to slide over the protrusions, but at the same time not allowing the latching members to be pulled off the protrusions in a direction perpendicular to the sliding motion. FIGS. 25 and 26 best illustrate one possible example of the channel, notch, indicator, and protrusion configuration. The latching members 402 are symmetrical so that they may be removed, inverted and then replaced, thereby changing the orientation of the latching members and allowing a right or left handed user to operate the device 400.

Referring now to FIG. 27 which illustrates an alternate embodiment 450 of the second embodiment of the present invention shown in FIG. 6. This alternate embodiment has a first elongated member 62 hingedly connected to a second elongated member 64. Both the first and second elongated members 62 and 64 each have a working head (not shown) and a finger engaging member 65 and 66 located opposite of the working head 63. A first lever 80 and second lever 100 are pivotally attachable to the finger engaging members 65 and 68, and are orientated so that the levers are facing each other. Additionally, latching members 452 are removably attachable to the finger engaging members 65 and 66. Each latching member 452 has a notch 458 for viewing an indicator located on the finger engaging members 65 and 66. The first and second elongated members 62 and 64 can be made from any suitable material having reflex memory.

Figure 28:
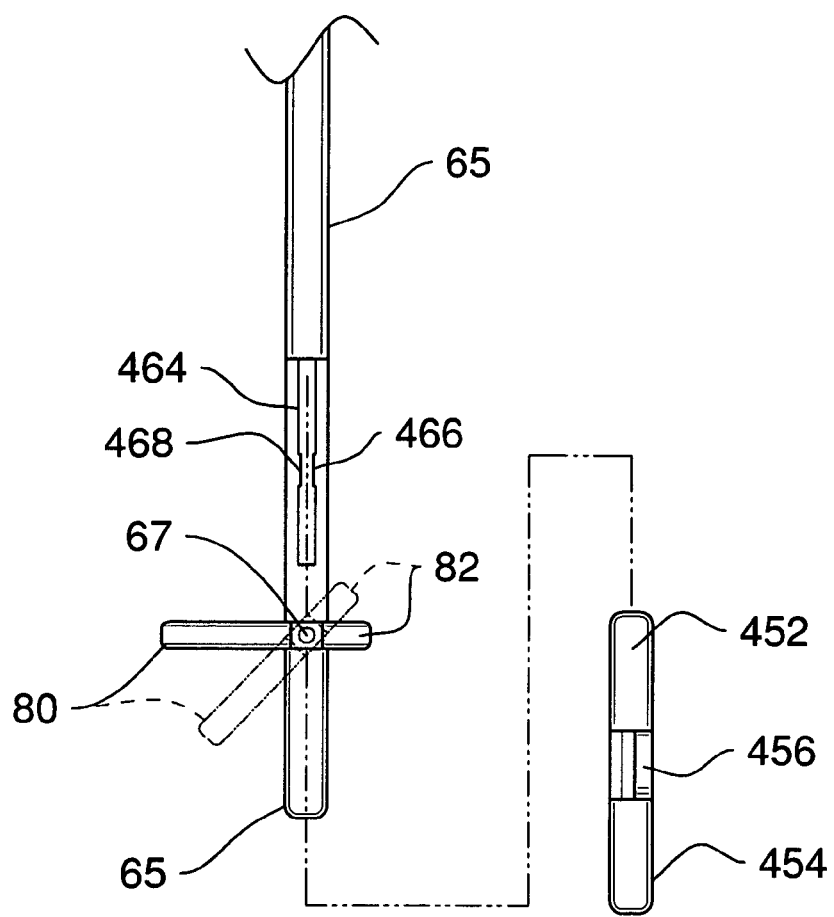
FIG. 28 is an exploded side elevational view of the alternate embodiment of the second embodiment of the present invention.

The levers 80 and 100 have an extended portion for easy operation by the fingers of a user, and are contoured to conform to the shape of the finger engaging members 65 and 66. A pivot pin 67 extends from the finger engaging members 65 and 66, and through levers 80 and 100, allowing the levers to rotate. The levers 80 and 100 have an extension 82 and 102 for retaining the first and second latching members 452 on the finger engaging members 65 and 66 when the levers are aligned with the longitudinal axis of the first and second elongated members 62 and 64. A notch 84 and 104 is defined in the levers 80 and 100 for allowing the latching members 452 to pass therethrough. When the levers 80 and 100 are rotated so they are perpendicular to the first and second elongated members 62 and 64, the extensions 82 and 102 are moved out of engagement with the latching members 452, and the notches 84 and 104 are exposed to the latching members, thereby allowing the latching members to slide through the notches and be removed from finger engaging members 65 and 66. This is best illustrated in FIG. 28.

The latching members 452 each have an elongated base 454 and a latch arm 456 extending out from each elongated base. The latch arms 452 feature a plurality of teeth 462, which are adapted to join and lock together when engaged. The teeth 462 are able to disengage when pulled apart by the flexing of the first and second elongated members 62 and 64 when an opposing force is applied to the finger engaging members 65 and 66.

The elongated base 454 of the latching members 452 each have a channel 460 running the length of the elongated base. The channels 460 are adapted to slide on and be retained by protrusions 464 extending out from the finger engaging members 65 and 66 and adjacent to the levers 80 and 100. The protrusions 464 each have an indicator 468 and 466 located on opposite sides of the protrusion. The indicators 468 and 466 have a marking or indicia thereon to indicate a right or left hand use. The marking or indicia can be, but not limited to, the letter "R" and "L". The arrangement of indicators 468 and 466 are opposite for finger engaging members 65 and 66, so that not similar indicators are facing the user. This allows the user to view, from either side, through the notch 458 what orientation the ambidextrous locking clamp 450 is set for, as best shown in FIG. 27 which illustrates a right and left handed orientation.

Figure 29:
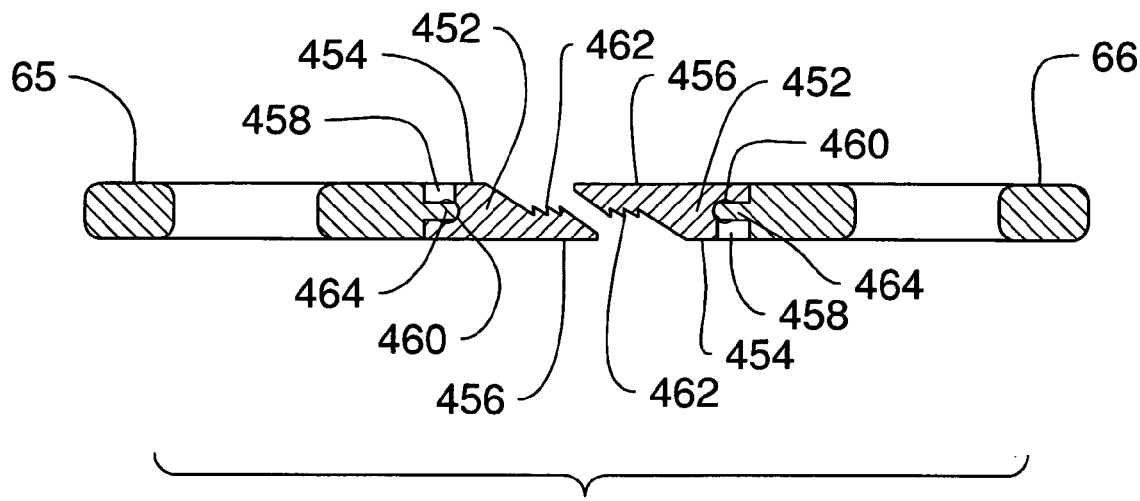
FIG. 29 is a cross-sectional view taken along the line 29-29 in FIG. 27 of the alternate embodiment of the second embodiment of the present invention.

The notch 458 is located on the elongated base 454 on the same side as the teeth 462. The notch 458 extends into the channel 460. When the latching members 452 are positioned on the protrusions 464, the notch 458 is located over either the indicator 468 or 466, depending on what orientation the latching members are set at for use either by a left or right handed user. The configuration of the channel 460 and the protrusions 464 allow the latching members 452 to slide over the protrusions, but at the same time not allowing the latching members to be pulled off the protrusions in a direction perpendicular to the sliding motion. The latching members 452 are symmetrical so that they may be removed, inverted and then replaced, thereby changing the orientation of the latching members and allowing a right or left handed user to operate the device 450. FIGS. 28 and 29 best illustrate one possible example of the channel, notch, indicator, and protrusion configuration.

Figure 30:
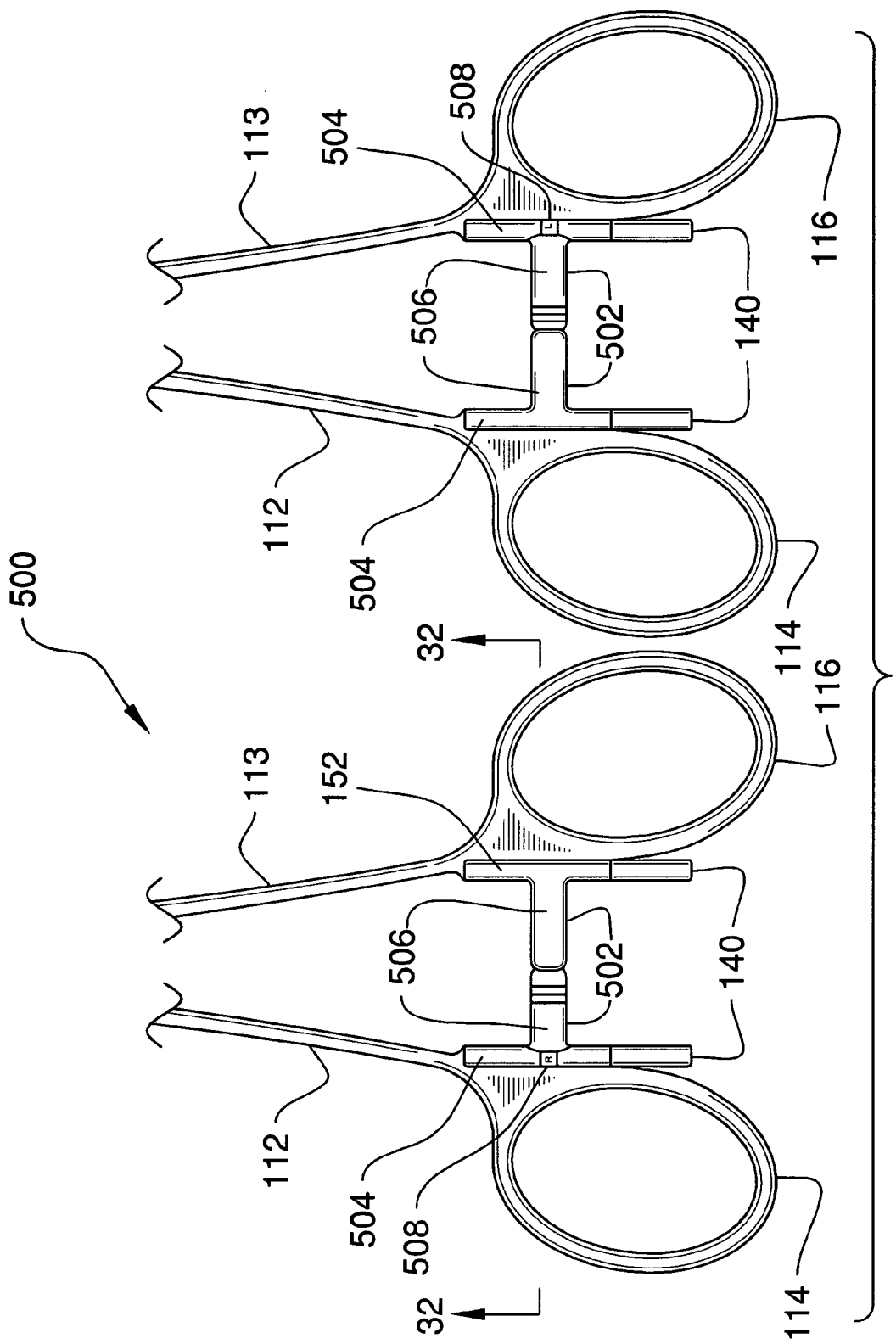
FIG. 30 is a front elevational view of an alternate embodiment of the third embodiment of the ambidextrous locking clamp system of FIG. 11.

Referring now to FIG. 30 which illustrates an alternate embodiment 500 of the third embodiment of the present invention shown in FIG. 11. This alternate embodiment has a first elongated member 112 hingedly connected to a second elongated member 113. Both the first and second elongated members 112 and 113 each have a working head (not shown)

and a finger engaging member 114 and 116 located opposite of the working head. Retaining caps 140 are threadably attachable to the finger engaging members 114 and 116, and are orientated so that the centerline of the caps are aligned with the longitudinal axis of the first and second elongated members 112 and 113. Additionally, latching members 502 are removably attachable to the finger engaging members 114 and 116. Each latching member 502 has a notch 508 for viewing an indicator located on the finger engaging members 114 and 116. The first and second elongated members 112 and 113 can be made from any suitable material having reflex memory.

Figure 31:
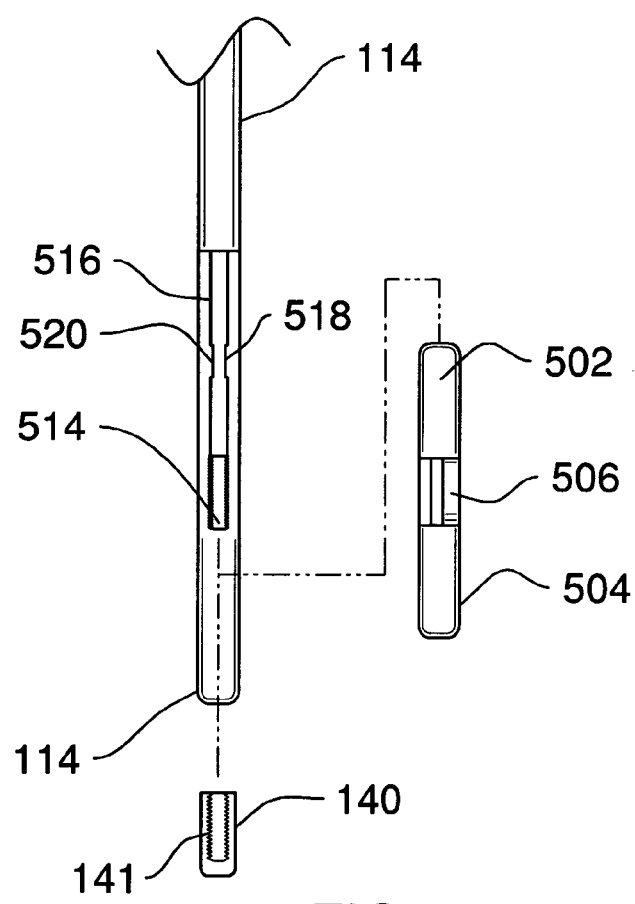
FIG. 31 is an exploded side elevational view of the alternate embodiment of the third embodiment of the present invention.

The retaining caps 140 have an internal threaded bore 141. The caps 140 are adapted to secure the first latching members 502 to the finger engaging members 114 and 116. The caps 140 are removably attachable to the finger engaging members 114 and 116 by screwing the caps onto a threaded stud 514 which extends out from a protrusion 516 of the finger engaging members 114 and 116, and adjacent the latching members 502. This is best illustrated in FIGS. 31. The caps 140 may have a smooth or textured surface, or a fastener driving configuration, such as a screw driver or allen wrench head.

The elongated base 504 of the latching members 502 each have a channel 512 running the length of the elongated base. The channels 512 are adapted to slide on and be retained by the protrusions 516 extending out from the finger engaging members 114 and 116 and adjacent to the threaded studs 514. The configuration of the channels 512 and the protrusions 516 allow the latching members 502 to slide over the protrusions, but at the same time not allowing the latching members to be pulled off the protrusions in a direction perpendicular to the sliding motion.

The protrusions 516 extend out from the finger engaging members 114 and 116, and are adapted to slidably receive the latching members 502. The threaded studs 514 extend out from the distal ends of protrusions 516. The protrusions 516 each have an indicator 518 and 520 located on opposite sides of the protrusion. The indicators 518 and 520 have a marking or indicia thereon to indicate a right or left hand use. The marking or indicia can be, but not limited to, the letter "R" and "L". The arrangement of indicators 518 and 520 are opposite for finger engaging members 114 and 116, so that not similar indicators are facing the user. This allows the user to view, from either side, through the notch 508 what orientation the ambidextrous locking clamp 500 is set for, as best shown in FIG. 31 which illustrates a right and left handed orientation.

The latching members 502 each have an elongated base 504 and a latch arm 506 extending out from each elongated base. The latch arms 506 feature a plurality of teeth 510, which are adapted to join and lock together when engaged. The teeth 510 are able to disengage when pulled apart by the flexing of the first and second elongated members 112 and 113 when an opposing force is applied to the finger engaging members 114 and 116. The latching members 502 are symmetrical so that they may be removed, inverted and then replaced, thereby changing the orientation of the latching members and allowing a right or left handed user to operate the device 500.

Figure 32:
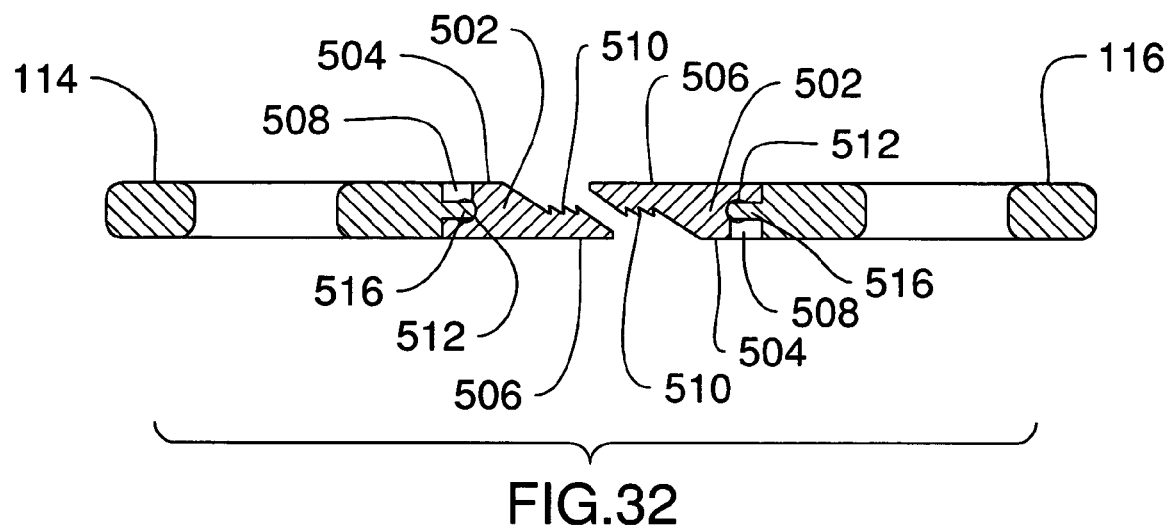
FIG. 32 is a cross-sectional view taken along the line 32-32 in FIG. 30 of the alternate embodiment of the third embodiment of the present invention.

The notch 508 is located on the elongated base 504 on the same side as the teeth 510. The notch 508 extends into the channel 512. When the latching members 502 are positioned on the protrusions 516, the notch 508 is located over either the indicator 518 or 520, depending on what orientation the latching members are set at for use either by a left or right handed user. FIGS. 31 and 32 best illustrate one possible example of the channel, notch, indicator, and protrusion configuration.

Figure 33:
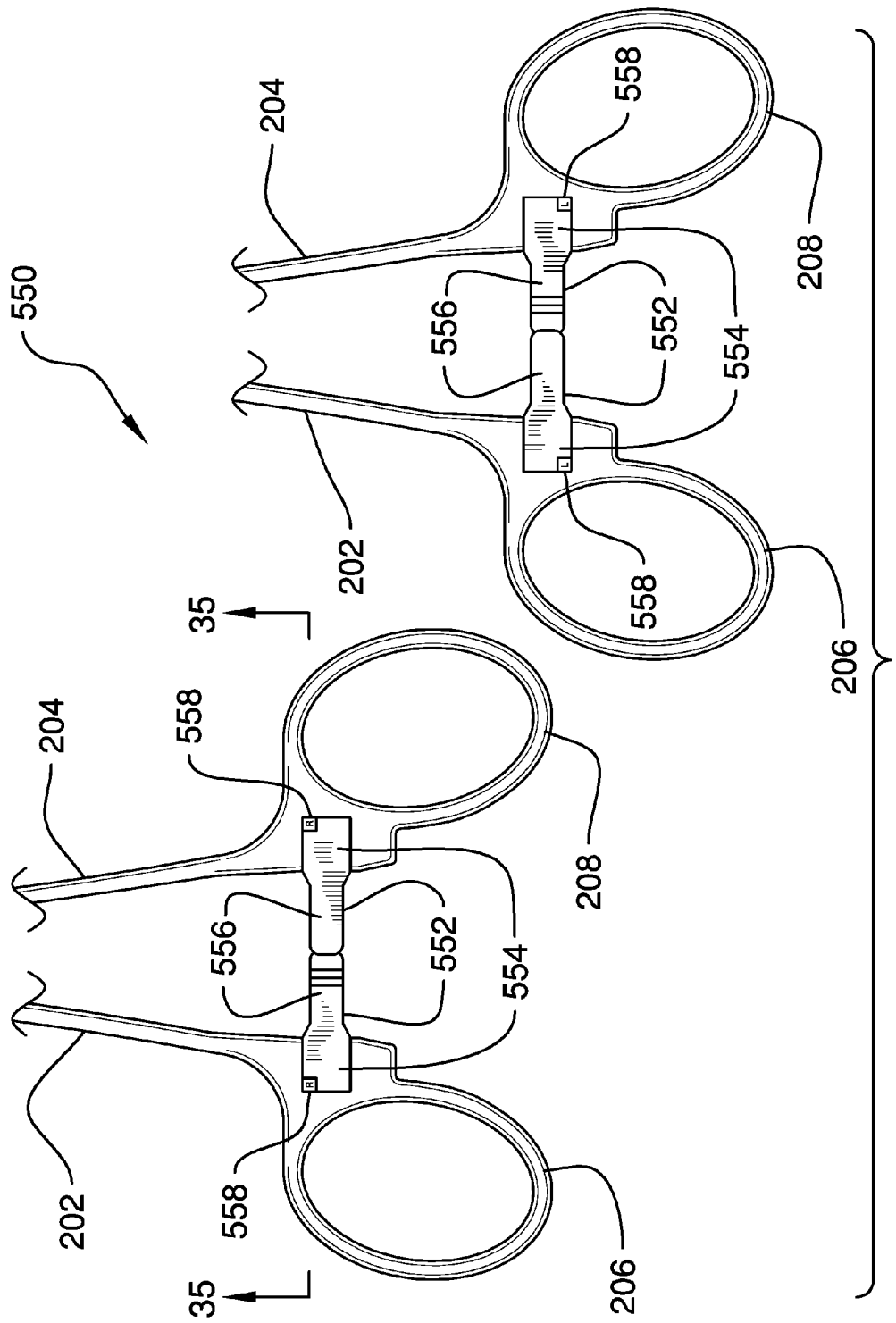
FIG. 33 is a front elevational view of an alternate embodiment of the fourth embodiment of the ambidextrous locking clamp system of FIG. 15.

Referring now to FIG. 33 which illustrates an alternate embodiment 550 of the fourth embodiment of the present invention shown in FIG. 15. This alternate embodiment has a first elongated member 202 hingedly connected to a second elongated member 204. Both the first and second elongated members 202 and 204 each have a working head (not shown) and a finger engaging member 206 and 208 located opposite of the working head. Additionally, latching members 552 are removably attachable to the finger engaging members 206 and 208. Each latching member 552 has a notch 558 for viewing an indicator located on the finger engaging members 206 and 208. The first and second elongated members 202 and 204 can be made from any suitable material having reflex memory.

The latching members 552 each have a base 554 and a latch arm 556 extending out from the base. The base 554 each have an aperture 562 defined therethrough. Threaded retaining pins 230 are insertable through threaded apertures 569 of the finger engaging members 206 and 208, and through the apertures 562 of the bases 554 of the latching members 552, as best illustrated in FIG. 34.

The threaded retaining pins 230 have a threaded section 231 featuring a driving head or detent, and a non-threaded section 234. The non-threaded sections 234 are adapted to be received through the threaded apertures 569 of the finger engaging members 206 and 208, and through the apertures 562 of the latching members 552. The threaded ends 231 engage the threaded apertures 569 to secure the retaining pins 230 in the finger engaging members 206 and 208, thereby securing the latching members 552 in notches 564 located in each of the finger engaging members. The latching members 552 are slidably insertable into notches 564 so that the base 554 rest in the notches and receives therein indicator ledges 568 located in the notches 564. The base 554 of the latching members 552 have a pair of channels 570 running the length of the base parallel with the longitudinal axis of the latch arms 552. As best illustrated in FIGS. 34, the channels 570 are adapted to receive a set of protrusions 566 which extend into the notches 564. The channel 570 and protrusion 566 connections are configured to retain the latching members 552 in the notches 564 and flush with the outer surface of the finger engaging members 206 and 208. Additionally, the channel 570 and protrusion 566 connections prevent the latching members 552 from rotating out of alignment with the notches 564.

The indicator ledges 568 have a marking or indicia thereon to indicate a right and left hand use. The markings or indicia can be, but not limited to, the letter "R" and "L". The markings are located at either end of the indicator ledge 568 and on both sides of the indicator ledge so that both sides are mirror images. The indicator ledges 568 are mirrored for finger engaging members 206 and 208, so that similar indicator ledges are facing the user. This allows the user to view, from either side, through the notches 558 what orientation the ambidextrous locking clamp 550 is set for, as best shown in FIG. 33 which illustrates a right and left handed orientation.

The notch 558 is located on one corner and on both sides of the base 554. The notch 558 extends through one channel 570 of the base 554. When the latching members 552 are positioned in the notches 564, the notches 558 are located over the indicator ledges 568 thereby exposing one of the markings on that side. The marking that is exposed depends on what orientation the latching members 552 are set at, for use either by a left or right handed user. The configuration of the channels 570, the protrusions 566, retaining pins 230, and the indicator ledges 568 allow the latching members 552 to slide into the notches 564 of the finger engaging members 206 and 208, but at the same time not allowing the latching members to be pulled out of the notches 564 in a direction perpendicular to the sliding motion. The latching members 552 are symmetrical so that they may be removed, inverted and then replaced, thereby changing the orientation of the latching members and allowing a right or left handed user to operate the device 550. FIGS. 34 and 35 best illustrate one possible example of the channel, retaining pin, notches, and indicator ledge configuration.

The latch arms 556 feature a plurality of teeth 560, which are adapted to join and lock together when engaged. The teeth 560 are able to disengage when pulled apart by the flexing of the first and second elongated members 202 and 204 when an opposing force is applied to the finger engaging members 206 and 208. The latching members 552 are symmetrical so that they may be removed, inverted and then replaced, thereby changing the orientation of the latching members and allowing a right or left handed user to operate the device 550. Furthermore, other configurations of the first and second latching members 552 may be used in place of the above described latching members.

Figure 36:
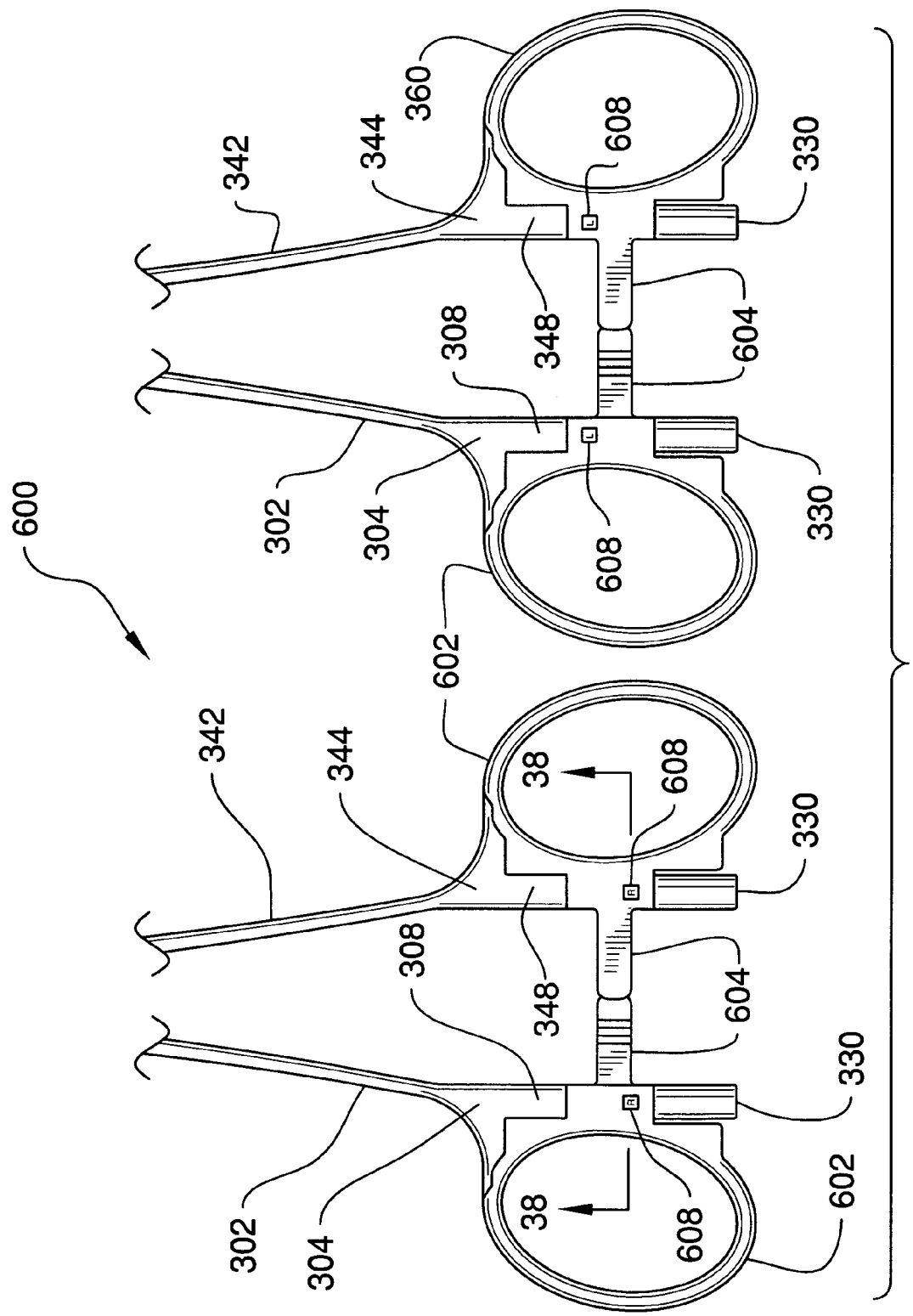
FIG. 36 is a front elevational view of an alternate embodiment of the fifth embodiment of the ambidextrous locking clamp system of FIG. 20.

Referring now to FIG. 36 which illustrates an alternate embodiment 600 of the fifth embodiment of the present invention shown in FIG. 20. This alternate embodiment has a first elongated member 302 hingedly connected to a second elongated member 342. Both the first and second elongated members 302 and 342 each have a working head (not shown) and a finger engaging member 602 located opposite of the working head. The first and second elongated members 302 and 342 each has a removable finger engaging member 602 located opposite of the working heads. Each removable finger engaging member 602 has a latching arm 604 extending out and towards each other. Retaining caps 330 are threadably attachable to the first and second elongated members 302 and 342, and are orientated so that the centerline of the caps are aligned with the longitudinal axis of the first and second elongated members. The retaining caps 330 can also be orientated in any alternate position to the first and second elongated members 302 and 342. The first and second retaining caps 330 are adapted to secure the finger engaging members 602 to the first and second elongated members 302 and 342. The first and second elongated members 302 and 342 can be made from any suitable material having reflex memory.

Figure 37:
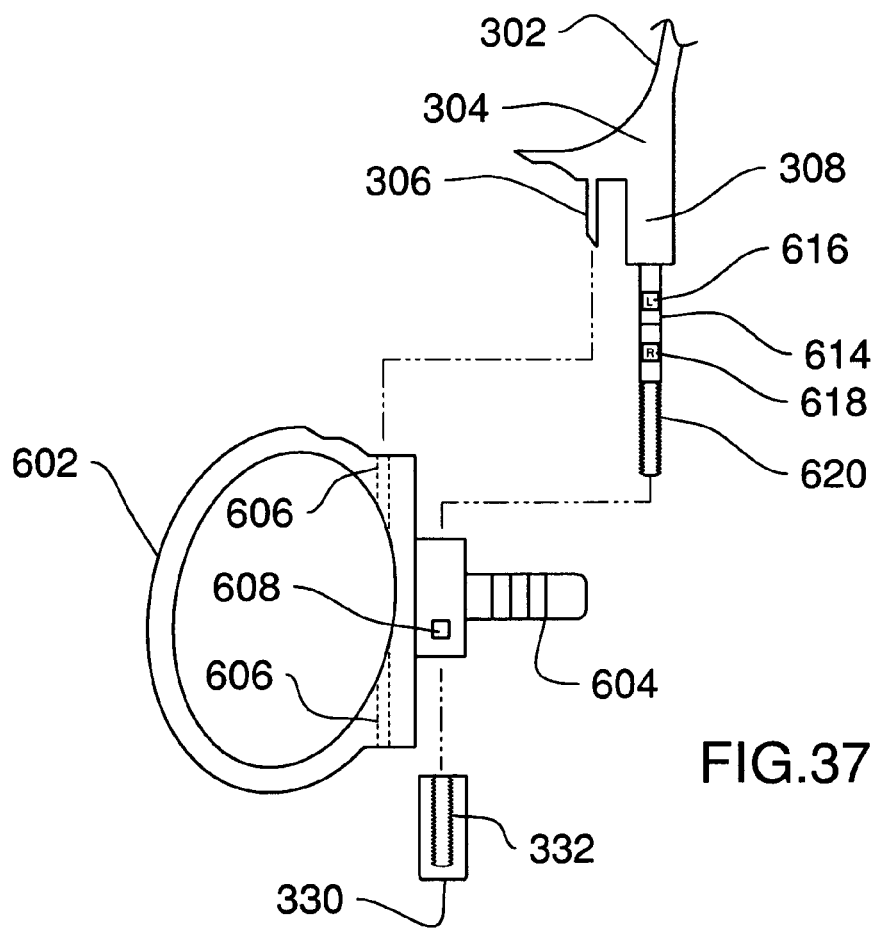
FIG. 37 is an exploded front elevational view of the alternate embodiment of the fifth embodiment of the present invention.

The first and second elongated members 302 and 342 each have a finger engaging member receiving assembly 304 and 344. The finger engaging member receiving assemblies 304 and 344 each have a protrusion 306, and a retaining rod 308 and 348. The retaining rods 308 and 348 include a stem 614 extending out therefrom, each with a threaded end 620. The stems 614 have indicators 616 and 618 located on both sides of the stem. The indicators 616 and 618 have a marking or indicia thereon to indicate a right or left hand use. The marking or indicia can be, but not limited to, the letter "R" and "L". The indicators 616 and 618 are located between the threaded end 620 and the retaining rods 304 and 308, so that similar indicators are facing the user. The indicators 616 and 618 are mirrored on both sides of the stem 614. This allows the user to view, from either side, through the notches 608 what orientation the ambidextrous locking clamp 500 is set for, as best shown in FIG. 36 which illustrates a right and left handed orientation. The retaining caps 330 have internally threaded bores 332 able to be threaded on to the treaded ends 620 of the stems 614. This is best illustrated in FIG. 37.

The finger engaging members 602 each have a bore 606 adapted to receive the protrusions 306 of the finger engaging member receiving assemblies 304 and 344, and a notch 608 for viewing an indicator located on the stem 614. The finger engaging members 602 also have an aperture 612 running parallel with the bores 606, which correspond to the configuration of the stems 614, and to the retaining rods 308 and 348. The finger engaging members 602 are positioned on to the protrusions 306 and 346, and to the stems 614, and are then secured to the finger engaging member receiving assemblies 304 and 344 by securing the retaining caps 330 on to the threaded ends 620 of stems 614, as best illustrated in FIG. 37.

The latching arms 604 each have a plurality of teeth 610, which are adapted to join and lock together when engaged. The teeth 610 are able to disengage when pulled apart by the flexing of the first and second elongated members 302 and 342 when an opposing force is applied to the finger engaging members 602. The finger engaging members 602 are symmetrical so that they may be removed, inverted and then replaced, thereby changing the orientation of the latching members and allowing a right or left handed user to operate the device 600. Furthermore, other configurations of the first and second finger engaging members 602 may be used in place of the above described latching members.

Figure 38:
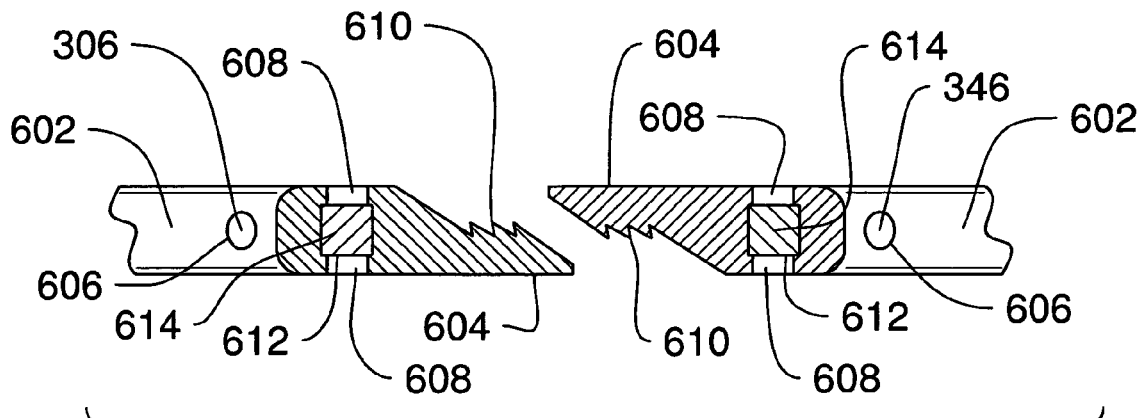
FIG. 38 is a cross-sectional view taken along the line 38-38 in FIG. 36 of the alternate embodiment of the fifth embodiment of the present invention.

The notches 608 are located on both sides of the finger engaging members 602, adjacent the latching arms 604. The notches 608 extend through the aperture 612. When the finger engaging members 602 are positioned on the stems 614, the notches 608 are located over either the indicators 616 or 618, depending on what orientation the finger engaging members are set at for use either by a left or right handed user. The configuration of the bores 606, the protrusions 306, apertures 612, and stems 614 allow the finger engaging members 602 to slide against the finger engaging member receiving assemblies 304, but at the same time not allowing the finger engaging members 602 to be pulled out in a direction perpendicular to the sliding motion. FIGS. 37 and 38 best illustrate one possible example of the channel, retaining pin, notches, and indicator ledge configuration.

In use, it can now be understood that either a right hand or left hand user can use the ambidextrous locking clamp system while having the ability to view through the use of indicators what the orientation the clamp is configured for, either right or left handed use. The user would remove and reverse the orientation of the removable latching member or the removable finger engaging member which features a latching arm. By doing this, the user can change the operational configuration of the ambidextrous locking device. The ambidextrous locking clamp system can use a variety of retaining means, such as, but not limited to, a rotating lever, a threaded cap, or a retaining pin. All of these retaining means can be used to secure the removable latching member or the removable finger engaging member from the elongated members.

While a preferred embodiment of the ambidextrous locking clamp system has been described in detail, it should be apparent that modifications and variations thereto are possible, all of which fall within the true spirit and scope of the invention. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention. For example, any suitable sturdy material may be used for the manufacture of the ambidextrous locking clamp system. And although manipulating objects with a tool having removable latching members have been described, it should be appreciated that the ambidextrous locking clamp system herein described is also suitable for all types of hand operated locking tools having a at least two hingedly connected arms.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. An ambidextrous locking clamp system for providing a user the ability to alter the configuration of a hand operated device allowing a right hand or left hand user to operate the device, said ambidextrous locking clamp system comprising:
    a first elongated member having a finger engaging member and a working head, said finger engaging member of said first elongated member having at least one first elongated member indicator for identifying at least one side of said ambidextrous locking clamp system;
    a second elongated member having a finger engaging member and a working head, said second elongated member being hingedly connected to said first elongated member, said finger engaging member of said second elongated member having at least one second elongated member indicator for identifying at least one side of said ambidextrous locking clamp system; and
    at least two latching members, wherein at least one of said latching members being removably attached to one of said first elongated member and said second elongated member, said latching members being adapted to removably engage each other, and each being adapted so that said first and second elongated member indicators of said first and second elongated members are each viewable through a corresponding latching member notch defined in a base of said latching member when said latching member is attached thereto respectively;
    wherein said first and second elongated members each comprising an elongated member notch, and at least one protrusion extending into said elongated member notch respectively, and wherein said latching members each having at least one channel defined along said base, said base being receivable in said elongated member notch of said first and second elongated members, said channel each having a shape corresponding to said protrusion of said first and second elongated members and being configured to receive said protrusion of said first and second elongated members respectively.

2. The ambidextrous locking clamp system of claim 1, wherein said latching members are slidably attached to said first and second elongated members.

3. The ambidextrous locking clamp system of claim 1, wherein said latching members each having a latching arm extending from said base, and wherein said channel defined along said base is parallel with a longitudinal axis of said latching arm.

4. The ambidextrous locking clamp system of claim 3, wherein each of said elongated member notches of said first and second elongated members further comprising an additional protrusion extending into said elongated member notch opposite said protrusion, and wherein each of said bases of said latching members further comprising an additional channel defined along said base parallel with said longitudinal axis of said latch arm and opposite of said channel, said additional channels being adapted to receive said additional protrusion of said first and second elongated members respectively.

5. The ambidextrous locking clamp system of claim 1 further comprising at least two retaining pins each being adapted to be inserted into said finger engaging members and said latching members of said first and second elongated members.

6. The ambidextrous locking clamp system of claim 5, wherein said latching members each having a bore defined therethrough for receiving said retaining pins.

7. The ambidextrous locking clamp system of claim 6, wherein said finger engaging members of said first and second elongated members having an elongated member notch adapted to receive said latching member therein.

8. The ambidextrous locking clamp system of claim 7, wherein said indicators of said first and second finger engaging members are each located on an indicator ledge receivable in a free end of said base of each of said latching members, and wherein said latching member notch of each of said latching members for viewing said indicators is configured to expose said indicator when said latching member is received in said elongated member notch.

9. The ambidextrous locking clamp system of claim 7, wherein said retaining pins having a threaded section and a non-threaded section.

10. The ambidextrous locking clamp system of claim 9, wherein said finger engaging members of said first and second elongated members each having a threaded bore adjacent said elongated member notches for receiving said threaded section of said retaining pins, thereby allowing said non-threaded section of said retaining pins to extend through said elongated member notches and through said bores of said latching members positioned in said elongated member notches.

11. The ambidextrous locking clamp system of claim 1, wherein said latching members having a channel defined therethrough, said channels being adapted to receive a protrusion extending out from said first and second elongated members.

12. The ambidextrous locking clamp system of claim 1, wherein said latching members having a plurality of teeth adapted to engage each other when said latching members are joined.

13. An ambidextrous locking clamp system comprising:
    a first elongated member having a finger engaging member, a first elongated member notch defined in said finger engaging member, and a working head opposite of said finger engaging member, said finger engaging member of said first elongated member having at least one indicator for identifying at least one side of said ambidextrous locking clamp system;
    a protrusion extending out from said finger engaging member of said first elongated member and into said first elongated member notch of said finger engaging member of said first elongated member;
    a second elongated member having a finger engaging member, a second elongated member notch defined in said finger engaging member, and a working head opposite of said finger engaging member, said second elongated member being hingedly connected to said first elongated member so said second elongated member notch of said second elongated member faces toward said first elongated member notch of said first elongated member, said finger engaging member of said second elongated member having at least one indicator for identifying at least one side of said ambidextrous locking clamp system;
    a protrusion extending out from said finger engaging member of said second elongated member and into said second elongated member notch of said finger engaging member of said second elongated member; and at least two latching members each having a base, a latching arm extending from said base, and a channel defined along said base parallel with a longitudinal axis of said latching arm, said bases being receivable in said first and second elongated member notches of said first and second elongated members respectively, said channels being adapted to receive said protrusions of said first and second elongated members respectively, said latching arms of said latching members each having a plurality of teeth adapted to removably engage each other, said latching members each being adapted so that said first and second elongated member indicators of said first and second elongated members are each viewable through a corresponding latching member notch defined in said base of said latching member when said latching member is attached thereto respectively;

wherein said protrusions of said first and second elongated members each extending along a length of said first and second elongated member notch parallel with the longitudinal axis of said latching member received in said first and second elongated member notch thereof respectively.

14. The ambidextrous locking clamp system of claim 13, wherein said protrusions being configured to slidably receive said latching members, while not allowing said latching members to be removed in a direction other than the direction of insertion.

15. The ambidextrous locking clamp system of claim 13, wherein each of said first and second elongated member notches of said first and second elongated members further comprising an additional protrusion extending into said first and second elongated member notch opposite said protrusion, and wherein each of said bases of said latching members further comprising an additional channel defined along said base parallel with a longitudinal axis of said latching arm and opposite of said channel and adapted to receive said additional protrusion of said first and second elongated members respectively.

16. The ambidextrous locking clamp system of claim 13 further comprising at least two retaining pins adapted to be inserted into said finger engaging members and said latching members of said first and second elongated members, said retaining pins retain said latching members in said first and second elongated member notch defined in said finger engaging members of said first and second elongated members.

17. The ambidextrous locking clamp system of claim 16, wherein said protrusions of said first and second elongated members are located along the interior of said first and second elongated member notches of said finger engaging members of said first and second elongated members.

18. The ambidextrous locking clamp system of claim 16, wherein said retaining pins each having a threaded section and a non-threaded section, and wherein said finger engaging members of said first and second elongated members each having a threaded bored adjacent said first and second elongated member notches for receiving said threaded section of said retaining pins, thereby allowing said non-threaded section of said retaining pins to extend through said first and second elongated member notches and through bores of said latching members positioned in said first and second elongated member notches.

19. The ambidextrous locking clamp system of claim 13, wherein said indicators of said first and second finger engaging members are each located on an indicator ledge receivable in a free end of said base of each of said latching members, and wherein said latching member notch of said latching members for viewing said indicators is configured to expose said indicator when said latching member is received in said first and second elongated member notch respectively.

20. An ambidextrous locking clamp comprising:
a first elongated member having a finger engaging member, a first elongated member notch defined in said finger engaging member, and a working head opposite of said finger engaging member, said finger engaging member of said first elongated member having at least one indicator for identifying at least one side of said ambidextrous locking clamp system;

a protrusion extending out from said finger engaging member of said first elongated member and into said first elongated member notch of finger engaging member of said first elongated member;

a second elongated member having a finger engaging member, a second elongated member notch defined in said finger engaging member, and a working head opposite of said finger engaging member, said second elongated member being hingedly connected to said first elongated member so said second elongated member notch of said second elongated member faces toward said first elongated member notch of said first elongated member, said finger engaging member of said second elongated member having at least one indicator for identifying at least one side of said ambidextrous locking clamp system;

a protrusion extending out from said finger engaging member of said second elongated member and into said second elongated member notch of finger engaging member of said second elongated member; and at least two latching members each having a base, a latching arm extending from said base, a channel defined along said base parallel with a longitudinal axis of said latching arm, and an opening defined in said base, said openings each corresponding to the shape of said first and second elongated member indicators and adapted to receive said first and second elongated member indicator when said latching member is received in said first and second elongated member notch respectively, said bases being receivable in said first and second elongated member notches of said first and second elongated members respectively, said channels being adapted to receive said protrusions of said first and second elongated members respectively, said latching arms of said latching members each having a plurality of teeth adapted to removably engage each other, and each being adapted so that said first and second elongated member indicators of said first and second elongated members are each viewable through a corresponding latching member notch defined in said base of said latching member when said latching member is attached thereto respectively;

wherein said protrusions of said first and second elongated members each extending along a length of said first and second elongated member notch parallel with the longitudinal axis of said latching member received in said first and second elongated member notch thereof respectively.

* * * * *